US012162920B2

(12) United States Patent
Zhang et al.

(10) Patent No.: US 12,162,920 B2
(45) Date of Patent: Dec. 10, 2024

(54) HINGE AREA AND USE OF SAME IN CONSTRUCTING CAR SKELETON

(71) Applicant: CHONGQING PRECISION BIOTECH COMPANY LIMITED, Chongqing (CN)

(72) Inventors: Wei Zhang, Chongqing (CN); JuanJuan Shan, Chongqing (CN); WenXu Zhao, Chongqing (CN); Jun Chen, Chongqing (CN); Xia Huang, Chongqing (CN); YongChun Zhao, Chongqing (CN); YanMin Xu, Chongqing (CN); QianZhen Zhang, Chongqing (CN)

(73) Assignee: CHONGQING PRECISION BIOTECH COMPANY LIMITED, Chongqing (CN)

( * ) Notice: Subject to any disclaimer, the term of this patent is extended or adjusted under 35 U.S.C. 154(b) by 1090 days.

(21) Appl. No.: 16/964,517

(22) PCT Filed: Dec. 6, 2018

(86) PCT No.: PCT/CN2018/119638
§ 371 (c)(1),
(2) Date: Jul. 23, 2020

(87) PCT Pub. No.: WO2019/144707
PCT Pub. Date: Aug. 1, 2019

(65) Prior Publication Data
US 2021/0107964 A1    Apr. 15, 2021

(30) Foreign Application Priority Data

Jan. 26, 2018 (CN) .......................... 201810075905.3
Jan. 26, 2018 (CN) .......................... 201810079289.9

(51) Int. Cl.
*C07K 14/705* (2006.01)
*A61K 39/00* (2006.01)
*C12N 15/86* (2006.01)

(52) U.S. Cl.
CPC ........ *C07K 14/705* (2013.01); *A61K 39/4611* (2023.05); *A61K 39/4631* (2023.05); *A61K 39/464493* (2023.05); *C12N 15/86* (2013.01); *A61K 2239/17* (2023.05); *A61K 2239/31* (2023.05); *A61K 2239/38* (2023.05); *A61K 2239/58* (2023.05); *C07K 2317/53* (2013.01); *C07K 2317/622* (2013.01); *C07K 2319/03* (2013.01)

(58) Field of Classification Search
CPC .............. C07K 14/705; C07K 2317/53; C07K 2317/622; C07K 2319/03; C07K 14/70521; C07K 14/7051; C12N 15/86; C12N 2740/16043; A61K 35/17; A61P 35/00
See application file for complete search history.

(56) References Cited

U.S. PATENT DOCUMENTS

| 2007/0031438 | A1 | 2/2007 | Junghans |
| 2013/0280285 | A1 | 10/2013 | Schonfeld et al. |

FOREIGN PATENT DOCUMENTS

| CN | 106456670 | A |   | 2/2017 |   |
| CN | 109306014 | A |   | 2/2019 |   |
| EP | 3115373 | A1 | * | 1/2017 | ......... C07K 14/7051 |
| WO | WO-2010037835 | A2 | * | 4/2010 | ................ A61P 1/04 |
| WO | 2017049166 | A1 |   | 3/2017 |   |
| WO | WO-2017176525 | A1 | * | 10/2017 | ............. A61K 35/14 |

OTHER PUBLICATIONS

English translation of Office Action in priority application CN 201810075905.3.
English translation of Office Action in priority application CN 201810079289.9.
English translation of Written Opinion of ISA for International Application No. PCT/CN2018/119638.
International Preliminary Report on Patentability for International Application No. PCT/CN2018/119638.
Jian, Yinxiu and HU, Wuliang. "AAY15457.1 CD 7 antigen [*Homo sapiens*]" GenBank, 28, Feb. 2006 (Feb. 28, 2006), entire document.
Flamar, A.L. et al. "AEL29442.1 monoclonal antibody 16E7_H [synthetic construct]" GenBank, Nov. 15, 2012 (Nov. 15, 2012), entire document.
De La Calle-Martin, O. et al. "AAK72403.1 mutant CD8 alpha antigen [*Homo sapiens*]" GenBank, Jul. 17, 2001 (Jul. 17, 2001), entire document.
Wei, S. et al. "T-cell antigen CD7 precursor [*Homo sapiens*]" NCBI Reference Sequence: NP_006128.1, Jul. 4, 2020, entire document.
Sempowski, Gregory D. et al., "Structure and Function of the CD7 Molecule" Critical Reviews, 19:331-348, 1999, entire document.
International Search Report of ISA for International Application No. PCT/CN2018/119638.
Written Opinion of ISA for International Application No. PCT/CN2018/119638.
Office Action in priority application CN 201810075905.3.
Office Action in priority application CN 201810079289.9.
Second Office Action in priority application CN 201810075905.3.
Second Office Action in priority application CN 201810079289.9.
JP Office Action dated Nov. 16, 2021 for Application No. JP2020-560528.

* cited by examiner

*Primary Examiner* — Julie Wu
*Assistant Examiner* — Francesca Edgingtongiordan
(74) *Attorney, Agent, or Firm* — JCIP; Joseph G. Chu

(57) ABSTRACT

Provided in the present invention are an improved hinge area and the use of same in constructing CAR skeleton. The amino acid sequence of the improved hinge area is as shown in SEQ ID NO.1 or SEQ ID NO.2 or SEQ ID NO.3, and the hinge area can prolong the survival of CAR-T cells in vivo and/or improve the capability of CAR-T cells to infiltrate tumors.

7 Claims, 5 Drawing Sheets

Specification includes a Sequence Listing.

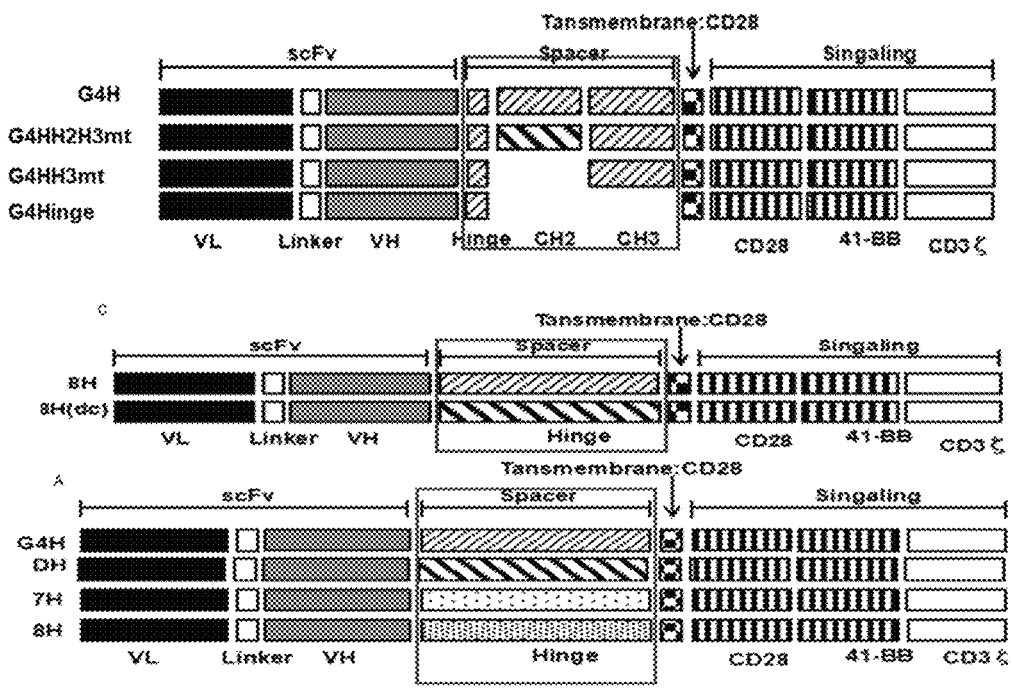

Figure 1

G4HH2H3 hinge region amino acid sequence (SEQ NO ID: 4)

ESKYGPPCPPCPAPEFLGGPSVFLFPPKPKDTLMISRTPEVTCVVVDVSQEDPEVQFN
WYVDGVEVHNAKTKPREEQFNSTYRVVSVLTVLHQDWLNGKEYKCKVSNKGLPSSIE
KTISKAKGQPREPQVYTLPPSQEEMTKNQVSLTCLVKGFYPSDIAVEWESNGQPENNY
KTTPPVLDSDGSFFLYSRLTVDKSRWQEGNVFSCSVMHEALHNHYTQKSLSLSLGK

G4HH2H3mt hinge region amino acid sequence (SEQ NO ID: 2)

ESKYGPPCPPCPAPPVA-GPSVFLFPPKPKDTLMISRTPEVTCVVVDVSQEDPEVQFN
WYVDGVEVHNAKTKPREEQFQSTYRVVSVLTVLHQDWLNGKEYKCKVSNKGLPSSIE
KTISKAKGQPREPQVYTLPPSQEEMTKNQVSLTCLVKGFYPSDIAVEWESNGQPENNY
KTTPPVLDSDGSFFLYSRLTVDKSRWQEGNVFSCSVMHEALHNHYTQKSLSLSLGK

7H hinge region amino acid sequence (SEQ NO ID: 1)

APPRASALPAPPTGSALPDPQTASALPDPPAASALP

8H hinge region amino acid sequence (SEQ NO ID: 5)

KPTTTPAPRPPTPAPTIASQPLSLRPEACRPAAGGAVHTRGLDFACD

8H(dc) hinge region amino acid sequence (SEQ NO ID: 3)

KPTTTPAPRPPTPAPTIASQPLSLRPEA-RPAAGGAVHTRGLDFA-D

Figure 2

SEQUENCE LISTING

```
<160> NUMBER OF SEQ ID NOS: 40

<210> SEQ ID NO 1
<211> LENGTH: 36
<212> TYPE: PRT
<213> ORGANISM: Artificial
<220> FEATURE:
<223> OTHER INFORMATION: 7H - Synthetic Construct

<400> SEQUENCE: 1

Ala Pro Pro Arg Ala Ser Ala Leu Pro Ala Pro Pro Thr Gly Ser Ala
1               5                   10                  15

Leu Pro Asp Pro Gln Thr Ala Ser Ala Leu Pro Asp Pro Ala Ala
            20                  25                  30

Ser Ala Leu Pro
        35

<210> SEQ ID NO 2
<211> LENGTH: 228
<212> TYPE: PRT
<213> ORGANISM: Artificial
<220> FEATURE:
```

<223> OTHER INFORMATION: G4HH2H3mt - Synthetic Construct

<400> SEQUENCE: 2

Glu Ser Lys Tyr Gly Pro Pro Cys Pro Pro Cys Pro Ala Pro Pro Val
1               5                   10                  15

Ala Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

Gln Glu Asp Pro Glu Val Gln Phe Asn Trp Tyr Val Asp Gly Val Glu
    50                  55                  60

Val His Asn Ala Lys Thr Lys Pro Arg Glu Glu Gln Phe Gln Ser Thr
65                  70                  75                  80

Tyr Arg Val Val Ser Val Leu Thr Val Leu His Gln Asp Trp Leu Asn
                85                  90                  95

Gly Lys Glu Tyr Lys Cys Lys Val Ser Asn Lys Gly Leu Pro Ser Ser
            100                 105                 110

Ile Glu Lys Thr Ile Ser Lys Ala Lys Gly Gln Pro Arg Glu Pro Gln
        115                 120                 125

Val Tyr Thr Leu Pro Pro Ser Gln Glu Glu Met Thr Lys Asn Gln Val
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Arg Leu Thr
            180                 185                 190

Val Asp Lys Ser Arg Trp Gln Glu Gly Asn Val Phe Ser Cys Ser Val
        195                 200                 205

Met His Glu Ala Leu His Asn His Tyr Thr Gln Lys Ser Leu Ser Leu
    210                 215                 220

Ser Leu Gly Lys
225

<210> SEQ ID NO 3
<211> LENGTH: 45
<212> TYPE: PRT
<213> ORGANISM: Artificial
<220> FEATURE:
<223> OTHER INFORMATION: 8H(dc) - Synthetic Construct

<400> SEQUENCE: 3

Lys Pro Thr Thr Thr Pro Ala Pro Arg Pro Pro Thr Pro Ala Pro Thr
1               5                   10                  15

Ile Ala Ser Gln Pro Leu Ser Leu Arg Pro Glu Ala Arg Pro Ala Ala
            20                  25                  30

Gly Gly Ala Val His Thr Arg Gly Leu Asp Phe Ala Asp
        35                  40                  45

<210> SEQ ID NO 4
<211> LENGTH: 229
<212> TYPE: PRT
<213> ORGANISM: Artificial
<220> FEATURE:
<223> OTHER INFORMATION: G4HH2H3 - Synthetic Construct

<400> SEQUENCE: 4

Glu Ser Lys Tyr Gly Pro Pro Cys Pro Pro Cys Pro Ala Pro Glu Phe

```
            1               5                   10                  15
          Leu Gly Gly Pro Ser Val Phe Leu Phe Pro Lys Pro Lys Asp Thr
                          20                  25                  30
          Leu Met Ile Ser Arg Thr Pro Glu Val Thr Cys Val Val Asp Val
                      35                  40                  45
          Ser Gln Glu Asp Pro Glu Val Gln Phe Asn Trp Tyr Val Asp Gly Val
           50                  55                  60
          Glu Val His Asn Ala Lys Thr Lys Pro Arg Glu Glu Gln Phe Asn Ser
           65                  70                  75                  80
          Thr Tyr Arg Val Val Ser Val Leu Thr Val Leu His Gln Asp Trp Leu
                              85                  90                  95
          Asn Gly Lys Glu Tyr Lys Cys Lys Val Ser Asn Lys Gly Leu Pro Ser
                          100                 105                 110
          Ser Ile Glu Lys Thr Ile Ser Lys Ala Lys Gly Gln Pro Arg Glu Pro
                      115                 120                 125
          Gln Val Tyr Thr Leu Pro Pro Ser Gln Glu Glu Met Thr Lys Asn Gln
                  130                 135                 140
          Val Ser Leu Thr Cys Leu Val Lys Gly Phe Tyr Pro Ser Asp Ile Ala
          145                 150                 155                 160
          Val Glu Trp Glu Ser Asn Gly Gln Pro Glu Asn Asn Tyr Lys Thr Thr
                              165                 170                 175
          Pro Pro Val Leu Asp Ser Asp Gly Ser Phe Phe Leu Tyr Ser Arg Leu
                          180                 185                 190
          Thr Val Asp Lys Ser Arg Trp Gln Glu Gly Asn Val Phe Ser Cys Ser
                      195                 200                 205
          Val Met His Glu Ala Leu His Asn His Tyr Thr Gln Lys Ser Leu Ser
                  210                 215                 220
          Leu Ser Leu Gly Lys
          225

<210> SEQ ID NO 5
<211> LENGTH: 47
<212> TYPE: PRT
<213> ORGANISM: Artificial
<220> FEATURE:
<223> OTHER INFORMATION: 8H - Synthetic Construct

<400> SEQUENCE: 5

Lys Pro Thr Thr Thr Pro Ala Pro Arg Pro Thr Pro Ala Pro Thr
          1               5                   10                  15
          Ile Ala Ser Gln Pro Leu Ser Leu Arg Pro Glu Ala Cys Arg Pro Ala
                          20                  25                  30
          Ala Gly Gly Ala Val His Thr Arg Gly Leu Asp Phe Ala Cys Asp
                      35                  40                  45

<210> SEQ ID NO 6
<211> LENGTH: 237
<212> TYPE: PRT
<213> ORGANISM: Artificial
<220> FEATURE:
<223> OTHER INFORMATION: PSCA-scFV - Synthetic Construct

<400> SEQUENCE: 6

Asp Ile Gln Leu Thr Gln Ser Pro Ser Ser Leu Ser Ala Ser Val Gly
          1               5                   10                  15
          Asp Arg Val Thr Ile Thr Cys Ser Ala Ser Ser Ser Val Arg Phe Ile
                          20                  25                  30
```

His Trp Tyr Gln Gln Lys Pro Gly Lys Ala Pro Lys Arg Leu Ile Tyr
                35                  40                  45

Asp Thr Ser Lys Leu Ala Ser Gly Val Pro Ser Arg Phe Ser Gly Ser
 50                  55                  60

Gly Ser Gly Thr Asp Phe Thr Leu Thr Ile Ser Ser Leu Gln Pro Glu
 65                  70                  75                  80

Asp Phe Ala Thr Tyr Tyr Cys Gln Gln Trp Ser Ser Pro Phe Thr
                 85                  90                  95

Phe Gly Gln Gly Thr Lys Val Glu Ile Lys Gly Ser Thr Ser Gly Ser
                100                 105                 110

Gly Lys Pro Gly Ser Gly Glu Gly Ser Thr Lys Gly Ser Glu Val Gln
            115                 120                 125

Leu Val Glu Ser Gly Gly Gly Leu Val Gln Pro Gly Gly Ser Leu Arg
130                 135                 140

Leu Ser Cys Ala Ala Ser Gly Phe Asn Ile Lys Asp Tyr Tyr Ile His
145                 150                 155                 160

Trp Val Arg Gln Ala Pro Gly Lys Gly Leu Glu Trp Val Ala Trp Ile
                165                 170                 175

Asp Pro Glu Asn Gly Asp Thr Glu Phe Val Pro Lys Phe Gln Gly Arg
            180                 185                 190

Ala Thr Ile Ser Ala Asp Thr Ser Lys Asn Thr Ala Tyr Leu Gln Met
        195                 200                 205

Asn Ser Leu Arg Ala Glu Asp Thr Ala Val Tyr Tyr Cys Lys Thr Gly
    210                 215                 220

Gly Phe Trp Gly Gln Gly Thr Leu Val Thr Val Ser Ser
225                 230                 235

<210> SEQ ID NO 7
<211> LENGTH: 246
<212> TYPE: PRT
<213> ORGANISM: Artificial
<220> FEATURE:
<223> OTHER INFORMATION: PSCA-scFV - Synthetic Construct

<400> SEQUENCE: 7

Asp Ile Gln Met Thr Gln Ser Pro Ser Ser Leu Ser Ala Ser Val Gly
1               5                   10                  15

Asp Arg Val Thr Ile Thr Cys Arg Thr Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Leu Lys Leu Asn Ser Gly Val Pro Ser Arg Phe Ser Gly
 50                  55                  60

Ser Gly Ser Gly Thr Asp Phe Thr Phe Thr Ile Ser Ser Leu Gln Pro
 65                  70                  75                  80

Glu Asp Ile Ala Thr Tyr Tyr Cys Gln Gln Ser Lys Thr Leu Pro Trp
                 85                  90                  95

Thr Phe Gly Gly Gly Thr Lys Val Glu Ile Lys Gly Ser Thr Ser Gly
                100                 105                 110

Ser Gly Lys Pro Gly Ser Gly Glu Gly Ser Thr Lys Gly Gln Val Lys
            115                 120                 125

Leu Gln Glu Ser Gly Gly Gly Leu Val Gln Pro Gly Gly Ser Leu Lys
130                 135                 140

Leu Ser Cys Val Ala Ser Gly Phe Thr Phe Ser Ser Tyr Thr Met Ser
145                 150                 155                 160

-continued

Trp Val Arg Arg Thr Pro Glu Lys Arg Leu Glu Trp Val Ala Tyr Ile
                165                 170                 175

His Asn Gly Gly Gly His Thr Tyr Tyr Pro Asp Thr Ile Lys Gly Arg
            180                 185                 190

Phe Thr Ile Ser Arg Asp Asn Ala Lys Asn Thr Leu Phe Leu Glu Met
        195                 200                 205

Ser Ser Leu Lys Ser Glu Asp Thr Ala Met Tyr Tyr Cys Thr Arg Arg
    210                 215                 220

Met Tyr Tyr Gly Asn Ser His Trp Tyr Phe Asp Val Trp Gly Ala Gly
225                 230                 235                 240

Thr Ser Val Thr Val Ser
            245

<210> SEQ ID NO 8
<211> LENGTH: 27
<212> TYPE: PRT
<213> ORGANISM: Artificial
<220> FEATURE:
<223> OTHER INFORMATION: CD28TM - Synthetic Construct

<400> SEQUENCE: 8

Phe Trp Val Leu Val Val Val Gly Gly Val Leu Ala Cys Tyr Ser Leu
1               5                   10                  15

Leu Val Thr Val Ala Phe Ile Ile Phe Trp Val
            20                  25

<210> SEQ ID NO 9
<211> LENGTH: 24
<212> TYPE: PRT
<213> ORGANISM: Artificial
<220> FEATURE:
<223> OTHER INFORMATION: CD8 TM - Synthetic Construct

<400> SEQUENCE: 9

Ile Tyr Ile Trp Ala Pro Leu Ala Gly Thr Cys Gly Val Leu Leu Leu
1               5                   10                  15

Ser Leu Val Ile Thr Leu Tyr Cys
            20

<210> SEQ ID NO 10
<211> LENGTH: 41
<212> TYPE: PRT
<213> ORGANISM: Artificial
<220> FEATURE:
<223> OTHER INFORMATION: CD28 - Synthetic Construct

<400> SEQUENCE: 10

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40

<210> SEQ ID NO 11
<211> LENGTH: 44
<212> TYPE: PRT
<213> ORGANISM: Artificial
<220> FEATURE:
<223> OTHER INFORMATION: CD137 - Synthetic Construct

<400> SEQUENCE: 11

```
Val Lys Arg Gly Arg Lys Leu Leu Tyr Ile Phe Lys Gln Pro Phe
1               5                   10                  15

Met Arg Pro Val Gln Thr Thr Gln Glu Glu Asp Gly Cys Ser Cys Arg
            20                  25                  30

Phe Pro Glu Glu Glu Glu Gly Gly Cys Glu Leu Arg
        35                  40
```

<210> SEQ ID NO 12
<211> LENGTH: 111
<212> TYPE: PRT
<213> ORGANISM: Artificial
<220> FEATURE:
<223> OTHER INFORMATION: CD3 - Synthetic Construct

<400> SEQUENCE: 12

```
Val Lys Phe Ser Arg Ser Ala Asp Ala Pro Ala Tyr Gln Gln Gly Gln
1               5                   10                  15

Asn Gln Leu Tyr Asn Glu Leu Asn Leu Gly Arg Arg Glu Glu Tyr Asp
            20                  25                  30

Val Leu Asp Lys Arg Arg Gly Arg Asp Pro Glu Met Gly Gly Lys Pro
        35                  40                  45

Arg Arg Lys Asn Pro Gln Glu Gly Leu Tyr Asn Glu Leu Gln Lys Asp
50                  55                  60

Lys Met Ala Glu Ala Tyr Ser Glu Ile Gly Met Lys Gly Glu Arg Arg
65                  70                  75                  80

Arg Gly Lys Gly His Asp Gly Leu Tyr Gln Gly Leu Ser Thr Ala Thr
                85                  90                  95

Lys Asp Thr Tyr Asp Ala Leu His Met Gln Ala Leu Pro Pro Arg
            100                 105                 110
```

<210> SEQ ID NO 13
<211> LENGTH: 496
<212> TYPE: PRT
<213> ORGANISM: Artificial
<220> FEATURE:
<223> OTHER INFORMATION: PSCA-CAR-7H - Synthetic Construct

<400> SEQUENCE: 13

```
Asp Ile Gln Leu Thr Gln Ser Pro Ser Ser Leu Ser Ala Ser Val Gly
1               5                   10                  15

Asp Arg Val Thr Ile Thr Cys Ser Ala Ser Ser Ser Val Arg Phe Ile
            20                  25                  30

His Trp Tyr Gln Gln Lys Pro Gly Lys Ala Pro Lys Arg Leu Ile Tyr
        35                  40                  45

Asp Thr Ser Lys Leu Ala Ser Gly Val Pro Ser Arg Phe Ser Gly Ser
50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Ser Ser Ser Pro Phe Thr
                85                  90                  95

Phe Gly Gln Gly Thr Lys Val Glu Ile Lys Gly Ser Thr Ser Gly Ser
            100                 105                 110

Gly Lys Pro Gly Ser Gly Glu Gly Ser Thr Lys Gly Ser Glu Val Gln
        115                 120                 125

Leu Val Glu Ser Gly Gly Gly Leu Val Gln Pro Gly Gly Ser Leu Arg
    130                 135                 140

Leu Ser Cys Ala Ala Ser Gly Phe Asn Ile Lys Asp Tyr Tyr Ile His
145                 150                 155                 160
```

Trp Val Arg Gln Ala Pro Gly Lys Gly Leu Glu Trp Val Ala Trp Ile
            165                 170                 175

Asp Pro Glu Asn Gly Asp Thr Glu Phe Val Pro Lys Phe Gln Gly Arg
            180                 185                 190

Ala Thr Ile Ser Ala Asp Thr Ser Lys Asn Thr Ala Tyr Leu Gln Met
            195                 200                 205

Asn Ser Leu Arg Ala Glu Asp Thr Ala Val Tyr Tyr Cys Lys Thr Gly
            210                 215                 220

Gly Phe Trp Gly Gln Gly Thr Leu Val Thr Val Ser Ser Ala Pro Pro
225                 230                 235                 240

Arg Ala Ser Ala Leu Pro Ala Pro Pro Thr Gly Ser Ala Leu Pro Asp
            245                 250                 255

Pro Gln Thr Ala Ser Ala Leu Pro Asp Pro Pro Ala Ala Ser Ala Leu
            260                 265                 270

Pro Phe Trp Val Leu Val Val Val Gly Gly Val Leu Ala Cys Tyr Ser
            275                 280                 285

Leu Leu Val Thr Val Ala Phe Ile Ile Phe Trp Val Arg Ser Lys Arg
            290                 295                 300

Ser Arg Leu Leu His Ser Asp Tyr Met Asn Met Thr Pro Arg Arg Pro
305                 310                 315                 320

Gly Pro Thr Arg Lys His Tyr Gln Pro Tyr Ala Pro Pro Arg Asp Phe
            325                 330                 335

Ala Ala Tyr Arg Ser Val Lys Arg Gly Arg Lys Lys Leu Leu Tyr Ile
            340                 345                 350

Phe Lys Gln Pro Phe Met Arg Pro Val Gln Thr Thr Gln Glu Glu Asp
            355                 360                 365

Gly Cys Ser Cys Arg Phe Pro Glu Glu Glu Gly Gly Cys Glu Leu
370                 375                 380

Arg Val Lys Phe Ser Arg Ser Ala Asp Ala Pro Ala Tyr Gln Gln Gly
385                 390                 395                 400

Gln Asn Gln Leu Tyr Asn Glu Leu Asn Leu Gly Arg Arg Glu Glu Tyr
            405                 410                 415

Asp Val Leu Asp Lys Arg Arg Gly Arg Asp Pro Glu Met Gly Gly Lys
            420                 425                 430

Pro Arg Arg Lys Asn Pro Gln Glu Gly Leu Tyr Asn Glu Leu Gln Lys
            435                 440                 445

Asp Lys Met Ala Glu Ala Tyr Ser Glu Ile Gly Met Lys Gly Glu Arg
            450                 455                 460

Arg Arg Gly Lys Gly His Asp Gly Leu Tyr Gln Gly Leu Ser Thr Ala
465                 470                 475                 480

Thr Lys Asp Thr Tyr Asp Ala Leu His Met Gln Ala Leu Pro Pro Arg
            485                 490                 495

<210> SEQ ID NO 14
<211> LENGTH: 452
<212> TYPE: PRT
<213> ORGANISM: Artificial
<220> FEATURE:
<223> OTHER INFORMATION: PSCA-CAR1 - Synthetic Construct

<400> SEQUENCE: 14

Asp Ile Gln Leu Thr Gln Ser Pro Ser Leu Ser Ala Ser Val Gly
1               5                   10                  15

Asp Arg Val Thr Ile Thr Cys Ser Ala Ser Ser Val Arg Phe Ile
            20                  25                  30

-continued

His Trp Tyr Gln Gln Lys Pro Gly Lys Ala Pro Lys Arg Leu Ile Tyr
            35                  40                  45

Asp Thr Ser Lys Leu Ala Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Ser Ser Pro Phe Thr
                85                  90                  95

Phe Gly Gln Gly Thr Lys Val Glu Ile Lys Gly Ser Thr Ser Gly Ser
                100                 105                 110

Gly Lys Pro Gly Ser Gly Glu Gly Ser Thr Lys Gly Ser Glu Val Gln
            115                 120                 125

Leu Val Glu Ser Gly Gly Gly Leu Val Gln Pro Gly Gly Ser Leu Arg
    130                 135                 140

Leu Ser Cys Ala Ala Ser Gly Phe Asn Ile Lys Asp Tyr Tyr Ile His
145                 150                 155                 160

Trp Val Arg Gln Ala Pro Gly Lys Gly Leu Glu Trp Val Ala Trp Ile
                165                 170                 175

Asp Pro Glu Asn Gly Asp Thr Glu Phe Val Pro Lys Phe Gln Gly Arg
            180                 185                 190

Ala Thr Ile Ser Ala Asp Thr Ser Lys Asn Thr Ala Tyr Leu Gln Met
    195                 200                 205

Asn Ser Leu Arg Ala Glu Asp Thr Ala Val Tyr Tyr Cys Lys Thr Gly
210                 215                 220

Gly Phe Trp Gly Gln Gly Thr Leu Val Thr Val Ser Ser Ala Pro Pro
225                 230                 235                 240

Arg Ala Ser Ala Leu Pro Ala Pro Pro Thr Gly Ser Ala Leu Pro Asp
                245                 250                 255

Pro Gln Thr Ala Ser Ala Leu Pro Asp Pro Pro Ala Ala Ser Ala Leu
            260                 265                 270

Pro Ile Tyr Ile Trp Ala Pro Leu Ala Gly Thr Cys Gly Val Leu Leu
    275                 280                 285

Leu Ser Leu Val Ile Thr Leu Tyr Cys Val Lys Arg Gly Arg Lys Lys
290                 295                 300

Leu Leu Tyr Ile Phe Lys Gln Pro Phe Met Arg Pro Val Gln Thr Thr
305                 310                 315                 320

Gln Glu Glu Asp Gly Cys Ser Cys Arg Phe Pro Glu Glu Glu Glu Gly
                325                 330                 335

Gly Cys Glu Leu Arg Val Lys Phe Ser Arg Ser Ala Asp Ala Pro Ala
            340                 345                 350

Tyr Gln Gln Gly Gln Asn Gln Leu Tyr Asn Glu Leu Asn Leu Gly Arg
    355                 360                 365

Arg Glu Glu Tyr Asp Val Leu Asp Lys Arg Arg Gly Arg Asp Pro Glu
370                 375                 380

Met Gly Gly Lys Pro Arg Arg Lys Asn Pro Gln Glu Gly Leu Tyr Asn
385                 390                 395                 400

Glu Leu Gln Lys Asp Lys Met Ala Glu Ala Tyr Ser Glu Ile Gly Met
                405                 410                 415

Lys Gly Glu Arg Arg Arg Gly Lys Gly His Asp Gly Leu Tyr Gln Gly
            420                 425                 430

Leu Ser Thr Ala Thr Lys Asp Thr Tyr Asp Ala Leu His Met Gln Ala
    435                 440                 445

Leu Pro Pro Arg
    450

<210> SEQ ID NO 15
<211> LENGTH: 452
<212> TYPE: PRT
<213> ORGANISM: Artificial
<220> FEATURE:
<223> OTHER INFORMATION: PSCA-CAR2 - Synthetic Construct

<400> SEQUENCE: 15

Asp Ile Gln Leu Thr Gln Ser Pro Ser Ser Leu Ser Ala Ser Val Gly
1               5                   10                  15

Asp Arg Val Thr Ile Thr Cys Ser Ala Ser Ser Val Arg Phe Ile
            20                  25                  30

His Trp Tyr Gln Gln Lys Pro Gly Lys Ala Pro Lys Arg Leu Ile Tyr
            35                  40                  45

Asp Thr Ser Lys Leu Ala Ser Gly Val Pro Ser Arg Phe Ser Gly Ser
        50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Ser Ser Ser Pro Phe Thr
                85                  90                  95

Phe Gly Gln Gly Thr Lys Val Glu Ile Lys Gly Ser Thr Ser Gly Ser
            100                 105                 110

Gly Lys Pro Gly Ser Gly Glu Gly Ser Thr Lys Gly Ser Glu Val Gln
        115                 120                 125

Leu Val Glu Ser Gly Gly Gly Leu Val Gln Pro Gly Gly Ser Leu Arg
130                 135                 140

Leu Ser Cys Ala Ala Ser Gly Phe Asn Ile Lys Asp Tyr Tyr Ile His
145                 150                 155                 160

Trp Val Arg Gln Ala Pro Gly Lys Gly Leu Glu Trp Val Ala Trp Ile
                165                 170                 175

Asp Pro Glu Asn Gly Asp Thr Glu Phe Val Pro Lys Phe Gln Gly Arg
            180                 185                 190

Ala Thr Ile Ser Ala Asp Thr Ser Lys Asn Thr Ala Tyr Leu Gln Met
        195                 200                 205

Asn Ser Leu Arg Ala Glu Asp Thr Ala Val Tyr Tyr Cys Lys Thr Gly
210                 215                 220

Gly Phe Trp Gly Gln Gly Thr Leu Val Thr Val Ser Ser Ala Pro Pro
225                 230                 235                 240

Arg Ala Ser Ala Leu Pro Ala Pro Pro Thr Gly Ser Ala Leu Pro Asp
                245                 250                 255

Pro Gln Thr Ala Ser Ala Leu Pro Asp Pro Pro Ala Ala Ser Ala Leu
            260                 265                 270

Pro Phe Trp Val Leu Val Val Val Gly Gly Val Leu Ala Cys Tyr Ser
        275                 280                 285

Leu Leu Val Thr Val Ala Phe Ile Ile Phe Trp Val Arg Ser Lys Arg
290                 295                 300

Ser Arg Leu Leu His Ser Asp Tyr Met Asn Met Thr Pro Arg Arg Pro
305                 310                 315                 320

Gly Pro Thr Arg Lys His Tyr Gln Pro Tyr Ala Pro Pro Arg Asp Phe
                325                 330                 335

Ala Ala Tyr Arg Ser Val Lys Phe Ser Arg Ser Ala Asp Ala Pro Ala
            340                 345                 350

Tyr Gln Gln Gly Gln Asn Gln Leu Tyr Asn Glu Leu Asn Leu Gly Arg
            355                 360                 365

Arg Glu Glu Tyr Asp Val Leu Asp Lys Arg Arg Gly Arg Asp Pro Glu
        370                 375                 380

Met Gly Gly Lys Pro Arg Arg Lys Asn Pro Gln Glu Gly Leu Tyr Asn
385                 390                 395                 400

Glu Leu Gln Lys Asp Lys Met Ala Glu Ala Tyr Ser Glu Ile Gly Met
                405                 410                 415

Lys Gly Glu Arg Arg Arg Gly Lys Gly His Asp Gly Leu Tyr Gln Gly
            420                 425                 430

Leu Ser Thr Ala Thr Lys Asp Thr Tyr Asp Ala Leu His Met Gln Ala
        435                 440                 445

Leu Pro Pro Arg
    450

<210> SEQ ID NO 16
<211> LENGTH: 688
<212> TYPE: PRT
<213> ORGANISM: Artificial
<220> FEATURE:
<223> OTHER INFORMATION: PSCA-CAR-G4HH2H3mt - Synthetic Construct

<400> SEQUENCE: 16

Asp Ile Gln Leu Thr Gln Ser Pro Ser Leu Ser Ala Ser Val Gly
1               5                   10                  15

Asp Arg Val Thr Ile Thr Cys Ser Ala Ser Ser Ser Val Arg Phe Ile
            20                  25                  30

His Trp Tyr Gln Gln Lys Pro Gly Lys Ala Pro Lys Arg Leu Ile Tyr
        35                  40                  45

Asp Thr Ser Lys Leu Ala Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Ser Ser Ser Pro Phe Thr
                85                  90                  95

Phe Gly Gln Gly Thr Lys Val Glu Ile Lys Gly Ser Thr Ser Gly Ser
            100                 105                 110

Gly Lys Pro Gly Ser Gly Glu Gly Ser Thr Lys Gly Ser Glu Val Gln
        115                 120                 125

Leu Val Glu Ser Gly Gly Gly Leu Val Gln Pro Gly Gly Ser Leu Arg
    130                 135                 140

Leu Ser Cys Ala Ala Ser Gly Phe Asn Ile Lys Asp Tyr Tyr Ile His
145                 150                 155                 160

Trp Val Arg Gln Ala Pro Gly Lys Gly Leu Glu Trp Val Ala Trp Ile
                165                 170                 175

Asp Pro Glu Asn Gly Asp Thr Glu Phe Val Pro Lys Phe Gln Gly Arg
            180                 185                 190

Ala Thr Ile Ser Ala Asp Thr Ser Lys Asn Thr Ala Tyr Leu Gln Met
        195                 200                 205

Asn Ser Leu Arg Ala Glu Asp Thr Ala Val Tyr Tyr Cys Lys Thr Gly
    210                 215                 220

Gly Phe Trp Gly Gln Gly Thr Leu Val Thr Val Ser Ser Glu Ser Lys
225                 230                 235                 240

Tyr Gly Pro Pro Cys Pro Pro Cys Pro Ala Pro Pro Val Ala Gly Pro
                245                 250                 255

```
Ser Val Phe Leu Phe Pro Pro Lys Pro Lys Asp Thr Leu Met Ile Ser
            260                 265                 270

Arg Thr Pro Glu Val Thr Cys Val Val Val Asp Val Ser Gln Glu Asp
        275                 280                 285

Pro Glu Val Gln Phe Asn Trp Tyr Val Asp Gly Val Glu Val His Asn
    290                 295                 300

Ala Lys Thr Lys Pro Arg Glu Glu Gln Phe Gln Ser Thr Tyr Arg Val
305                 310                 315                 320

Val Ser Val Leu Thr Val Leu His Gln Asp Trp Leu Asn Gly Lys Glu
                325                 330                 335

Tyr Lys Cys Lys Val Ser Asn Lys Gly Leu Pro Ser Ser Ile Glu Lys
            340                 345                 350

Thr Ile Ser Lys Ala Lys Gly Gln Pro Arg Glu Pro Gln Val Tyr Thr
        355                 360                 365

Leu Pro Pro Ser Gln Glu Glu Met Thr Lys Asn Gln Val Ser Leu Thr
    370                 375                 380

Cys Leu Val Lys Gly Phe Tyr Pro Ser Asp Ile Ala Val Glu Trp Glu
385                 390                 395                 400

Ser Asn Gly Gln Pro Glu Asn Asn Tyr Lys Thr Thr Pro Pro Val Leu
                405                 410                 415

Asp Ser Asp Gly Ser Phe Phe Leu Tyr Ser Arg Leu Thr Val Asp Lys
            420                 425                 430

Ser Arg Trp Gln Glu Gly Asn Val Phe Ser Cys Ser Val Met His Glu
        435                 440                 445

Ala Leu His Asn His Tyr Thr Gln Lys Ser Leu Ser Leu Ser Leu Gly
    450                 455                 460

Lys Phe Trp Val Leu Val Val Gly Gly Val Leu Ala Cys Tyr Ser
465                 470                 475                 480

Leu Leu Val Thr Val Ala Phe Ile Ile Phe Trp Val Arg Ser Lys Arg
                485                 490                 495

Ser Arg Leu Leu His Ser Asp Tyr Met Asn Met Thr Pro Arg Arg Pro
            500                 505                 510

Gly Pro Thr Arg Lys His Tyr Gln Pro Tyr Ala Pro Pro Arg Asp Phe
        515                 520                 525

Ala Ala Tyr Arg Ser Val Lys Arg Gly Arg Lys Lys Leu Leu Tyr Ile
    530                 535                 540

Phe Lys Gln Pro Phe Met Arg Pro Val Gln Thr Thr Gln Glu Glu Asp
545                 550                 555                 560

Gly Cys Ser Cys Arg Phe Pro Glu Glu Glu Gly Gly Cys Glu Leu
                565                 570                 575

Arg Val Lys Phe Ser Arg Ser Ala Asp Ala Pro Ala Tyr Gln Gln Gly
            580                 585                 590

Gln Asn Gln Leu Tyr Asn Glu Leu Asn Leu Gly Arg Arg Glu Glu Tyr
        595                 600                 605

Asp Val Leu Asp Lys Arg Arg Gly Arg Asp Pro Glu Met Gly Gly Lys
    610                 615                 620

Pro Arg Arg Lys Asn Pro Gln Glu Gly Leu Tyr Asn Glu Leu Gln Lys
625                 630                 635                 640

Asp Lys Met Ala Glu Ala Tyr Ser Glu Ile Gly Met Lys Gly Glu Arg
                645                 650                 655

Arg Arg Gly Lys Gly His Asp Gly Leu Tyr Gln Gly Leu Ser Thr Ala
            660                 665                 670

Thr Lys Asp Thr Tyr Asp Ala Leu His Met Gln Ala Leu Pro Pro Arg
```

<210> SEQ ID NO 17
<211> LENGTH: 644
<212> TYPE: PRT
<213> ORGANISM: Artificial
<220> FEATURE:
<223> OTHER INFORMATION: PSCA-CAR3 - Synthetic Construct

<400> SEQUENCE: 17

Asp Ile Gln Leu Thr Gln Ser Pro Ser Ser Leu Ser Ala Ser Val Gly
1               5                   10                  15

Asp Arg Val Thr Ile Thr Cys Ser Ala Ser Ser Val Arg Phe Ile
            20                  25                  30

His Trp Tyr Gln Gln Lys Pro Gly Lys Ala Pro Lys Arg Leu Ile Tyr
        35                  40                  45

Asp Thr Ser Lys Leu Ala Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Ser Ser Pro Phe Thr
                85                  90                  95

Phe Gly Gln Gly Thr Lys Val Glu Ile Lys Gly Ser Thr Ser Gly Ser
            100                 105                 110

Gly Lys Pro Gly Ser Gly Glu Gly Ser Thr Lys Gly Ser Glu Val Gln
        115                 120                 125

Leu Val Glu Ser Gly Gly Gly Leu Val Gln Pro Gly Gly Ser Leu Arg
130                 135                 140

Leu Ser Cys Ala Ala Ser Gly Phe Asn Ile Lys Asp Tyr Tyr Ile His
145                 150                 155                 160

Trp Val Arg Gln Ala Pro Gly Lys Gly Leu Glu Trp Val Ala Trp Ile
                165                 170                 175

Asp Pro Glu Asn Gly Asp Thr Glu Phe Val Pro Lys Phe Gln Gly Arg
            180                 185                 190

Ala Thr Ile Ser Ala Asp Thr Ser Lys Asn Thr Ala Tyr Leu Gln Met
        195                 200                 205

Asn Ser Leu Arg Ala Glu Asp Thr Ala Val Tyr Tyr Cys Lys Thr Gly
    210                 215                 220

Gly Phe Trp Gly Gln Gly Thr Leu Val Thr Val Ser Ser Glu Ser Lys
225                 230                 235                 240

Tyr Gly Pro Pro Cys Pro Pro Cys Pro Ala Pro Val Ala Gly Pro
                245                 250                 255

Ser Val Phe Leu Phe Pro Pro Lys Pro Lys Asp Thr Leu Met Ile Ser
            260                 265                 270

Arg Thr Pro Glu Val Thr Cys Val Val Val Asp Val Ser Gln Glu Asp
        275                 280                 285

Pro Glu Val Gln Phe Asn Trp Tyr Val Asp Gly Val Glu Val His Asn
    290                 295                 300

Ala Lys Thr Lys Pro Arg Glu Glu Gln Phe Gln Ser Thr Tyr Arg Val
305                 310                 315                 320

Val Ser Val Leu Thr Val Leu His Gln Asp Trp Leu Asn Gly Lys Glu
                325                 330                 335

Tyr Lys Cys Lys Val Ser Asn Lys Gly Leu Pro Ser Ser Ile Glu Lys
            340                 345                 350

Thr Ile Ser Lys Ala Lys Gly Gln Pro Arg Glu Pro Gln Val Tyr Thr

```
                355                 360                 365
Leu Pro Pro Ser Gln Glu Glu Met Thr Lys Asn Gln Val Ser Leu Thr
            370                 375                 380

Cys Leu Val Lys Gly Phe Tyr Pro Ser Asp Ile Ala Val Glu Trp Glu
385                 390                 395                 400

Ser Asn Gly Gln Pro Glu Asn Asn Tyr Lys Thr Thr Pro Pro Val Leu
                405                 410                 415

Asp Ser Asp Gly Ser Phe Phe Leu Tyr Ser Arg Leu Thr Val Asp Lys
            420                 425                 430

Ser Arg Trp Gln Glu Gly Asn Val Phe Ser Cys Ser Val Met His Glu
        435                 440                 445

Ala Leu His Asn His Tyr Thr Gln Lys Ser Leu Ser Leu Ser Leu Gly
    450                 455                 460

Lys Ile Tyr Ile Trp Ala Pro Leu Ala Gly Thr Cys Gly Val Leu Leu
465                 470                 475                 480

Leu Ser Leu Val Ile Thr Leu Tyr Cys Val Lys Arg Gly Arg Lys Lys
                485                 490                 495

Leu Leu Tyr Ile Phe Lys Gln Pro Phe Met Arg Pro Val Gln Thr Thr
            500                 505                 510

Gln Glu Glu Asp Gly Cys Ser Cys Arg Phe Pro Glu Glu Glu Glu Gly
        515                 520                 525

Gly Cys Glu Leu Arg Val Lys Phe Ser Arg Ser Ala Asp Ala Pro Ala
    530                 535                 540

Tyr Gln Gln Gly Gln Asn Gln Leu Tyr Asn Glu Leu Asn Leu Gly Arg
545                 550                 555                 560

Arg Glu Glu Tyr Asp Val Leu Asp Lys Arg Arg Gly Arg Asp Pro Glu
                565                 570                 575

Met Gly Gly Lys Pro Arg Arg Lys Asn Pro Gln Glu Gly Leu Tyr Asn
            580                 585                 590

Glu Leu Gln Lys Asp Lys Met Ala Glu Ala Tyr Ser Glu Ile Gly Met
        595                 600                 605

Lys Gly Glu Arg Arg Arg Gly Lys Gly His Asp Gly Leu Tyr Gln Gly
    610                 615                 620

Leu Ser Thr Ala Thr Lys Asp Thr Tyr Asp Ala Leu His Met Gln Ala
625                 630                 635                 640

Leu Pro Pro Arg

<210> SEQ ID NO 18
<211> LENGTH: 644
<212> TYPE: PRT
<213> ORGANISM: Artificial
<220> FEATURE:
<223> OTHER INFORMATION: PSCA-CAR4 - Synthetic Construct

<400> SEQUENCE: 18

Asp Ile Gln Leu Thr Gln Ser Pro Ser Ser Leu Ser Ala Ser Val Gly
1               5                   10                  15

Asp Arg Val Thr Ile Thr Cys Ser Ala Ser Ser Ser Val Arg Phe Ile
            20                  25                  30

His Trp Tyr Gln Gln Lys Pro Gly Lys Ala Pro Lys Arg Leu Ile Tyr
        35                  40                  45

Asp Thr Ser Lys Leu Ala Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80
```

```
Asp Phe Ala Thr Tyr Tyr Cys Gln Gln Trp Ser Ser Pro Phe Thr
                85                  90                  95

Phe Gly Gln Gly Thr Lys Val Glu Ile Lys Gly Ser Thr Ser Gly
            100                 105                 110

Ser Gly Lys Pro Gly Ser Gly Glu Gly Ser Thr Lys Gly Ser Glu Val Gln
        115                 120                 125

Leu Val Glu Ser Gly Gly Gly Leu Val Gln Pro Gly Gly Ser Leu Arg
        130                 135                 140

Leu Ser Cys Ala Ala Ser Gly Phe Asn Ile Lys Asp Tyr Tyr Ile His
145                 150                 155                 160

Trp Val Arg Gln Ala Pro Gly Lys Gly Leu Glu Trp Val Ala Trp Ile
                165                 170                 175

Asp Pro Glu Asn Gly Asp Thr Glu Phe Val Pro Lys Phe Gln Gly Arg
            180                 185                 190

Ala Thr Ile Ser Ala Asp Thr Ser Lys Asn Thr Ala Tyr Leu Gln Met
        195                 200                 205

Asn Ser Leu Arg Ala Glu Asp Thr Ala Val Tyr Tyr Cys Lys Thr Gly
        210                 215                 220

Gly Phe Trp Gly Gln Gly Thr Leu Val Thr Val Ser Ser Glu Ser Lys
225                 230                 235                 240

Tyr Gly Pro Pro Cys Pro Pro Cys Pro Ala Pro Pro Val Ala Gly Pro
                245                 250                 255

Ser Val Phe Leu Phe Pro Pro Lys Pro Lys Asp Thr Leu Met Ile Ser
            260                 265                 270

Arg Thr Pro Glu Val Thr Cys Val Val Val Asp Val Ser Gln Glu Asp
        275                 280                 285

Pro Glu Val Gln Phe Asn Trp Tyr Val Asp Gly Val Glu Val His Asn
        290                 295                 300

Ala Lys Thr Lys Pro Arg Glu Glu Gln Phe Gln Ser Thr Tyr Arg Val
305                 310                 315                 320

Val Ser Val Leu Thr Val Leu His Gln Asp Trp Leu Asn Gly Lys Glu
                325                 330                 335

Tyr Lys Cys Lys Val Ser Asn Lys Gly Leu Pro Ser Ser Ile Glu Lys
            340                 345                 350

Thr Ile Ser Lys Ala Lys Gly Gln Pro Arg Glu Pro Gln Val Tyr Thr
        355                 360                 365

Leu Pro Pro Ser Gln Glu Glu Met Thr Lys Asn Gln Val Ser Leu Thr
        370                 375                 380

Cys Leu Val Lys Gly Phe Tyr Pro Ser Asp Ile Ala Val Glu Trp Glu
385                 390                 395                 400

Ser Asn Gly Gln Pro Glu Asn Asn Tyr Lys Thr Thr Pro Pro Val Leu
                405                 410                 415

Asp Ser Asp Gly Ser Phe Phe Leu Tyr Ser Arg Leu Thr Val Asp Lys
            420                 425                 430

Ser Arg Trp Gln Glu Gly Asn Val Phe Ser Cys Ser Val Met His Glu
        435                 440                 445

Ala Leu His Asn His Tyr Thr Gln Lys Ser Leu Ser Leu Ser Leu Gly
        450                 455                 460

Lys Phe Trp Val Leu Val Val Gly Gly Val Leu Ala Cys Tyr Ser
465                 470                 475                 480

Leu Leu Val Thr Val Ala Phe Ile Ile Phe Trp Val Arg Ser Lys Arg
                485                 490                 495
```

```
Ser Arg Leu Leu His Ser Asp Tyr Met Asn Met Thr Pro Arg Arg Pro
            500                 505                 510

Gly Pro Thr Arg Lys His Tyr Gln Pro Tyr Ala Pro Arg Asp Phe
        515                 520                 525

Ala Ala Tyr Arg Ser Val Lys Phe Ser Arg Ser Ala Asp Ala Pro Ala
        530                 535                 540

Tyr Gln Gln Gly Gln Asn Gln Leu Tyr Asn Glu Leu Asn Leu Gly Arg
545                 550                 555                 560

Arg Glu Glu Tyr Asp Val Leu Asp Lys Arg Gly Arg Asp Pro Glu
                565                 570                 575

Met Gly Gly Lys Pro Arg Arg Lys Asn Pro Gln Glu Gly Leu Tyr Asn
            580                 585                 590

Glu Leu Gln Lys Asp Lys Met Ala Glu Ala Tyr Ser Glu Ile Gly Met
            595                 600                 605

Lys Gly Glu Arg Arg Arg Gly Lys Gly His Asp Gly Leu Tyr Gln Gly
            610                 615                 620

Leu Ser Thr Ala Thr Lys Asp Thr Tyr Asp Ala Leu His Met Gln Ala
625                 630                 635                 640

Leu Pro Pro Arg

<210> SEQ ID NO 19
<211> LENGTH: 63
<212> TYPE: DNA
<213> ORGANISM: Artificial
<220> FEATURE:
<223> OTHER INFORMATION: Leader Peptide - Synthetic Construct

<400> SEQUENCE: 19
atggcactgc cagtgaccgc cctgctgctg cccctggcac tgctgctgca cgcagctcgg      60
cct                                                                   63

<210> SEQ ID NO 20
<211> LENGTH: 684
<212> TYPE: DNA
<213> ORGANISM: Artificial
<220> FEATURE:
<223> OTHER INFORMATION: G4HH2H3mt - Synthetic Construct

<400> SEQUENCE: 20
gaaagcaaat atggcccgcc gtgcccgccg tgccggcgc cgccggtggc gggcccgagc       60
gtgtttctgt ttccgccgaa accgaaagat accctgatga ttagccgcac cccggaagtg    120
acctgcgtgg tggtggatgt gagccaggaa gatccggaag tgcagtttaa ctggtatgtg    180
gatggcgtgg aagtgcataa cgcgaaaacc aaaccgcgcg aagaacagtt tcagagcacc    240
tatcgcgtgg tgagcgtgct gaccgtgctg catcaggatt ggctgaacgg caaagaatat    300
aaatgcaaag tgagcaacaa aggcctgccg agcagcattg aaaaaaccat tagcaaagcg    360
aaaggccagc cgcgcgaacc gcaggtgtat accctgccgc cgagccagga agaaatgacc    420
aaaaaccagg tgagcctgac ctgcctggtg aaaggctttt atccgagcga tattgcggtg    480
gaatgggaaa gcaacggcca gccggaaaac aactataaaa ccaccccgcc ggtgctggat    540
agcgatggca gcttttttct gtatagccgc ctgaccgtgg ataaaagccg ctggcaggaa    600
ggcaacgtgt ttagctgcag cgtgatgcat gaagcgctgc ataaccatta tacccagaaa    660
agcctgagcc tgagcctggg caaa                                            684

<210> SEQ ID NO 21
```

```
<211> LENGTH: 108
<212> TYPE: DNA
<213> ORGANISM: Artificial
<220> FEATURE:
<223> OTHER INFORMATION: 7H - Synthetic Construct

<400> SEQUENCE: 21
gcgccgccgc gcgcgagcgc gctgccggcg ccgccgaccg gcagcgcgct gccggatccg      60
cagaccgcga gcgcgctgcc ggatccgccg gcggcgagcg cgctgccg                  108

<210> SEQ ID NO 22
<211> LENGTH: 30
<212> TYPE: DNA
<213> ORGANISM: Artificial
<220> FEATURE:
<223> OTHER INFORMATION: Forward Primer - Synthetic Construct

<400> SEQUENCE: 22
atcgctagca tggccctgcc agtgaccgcc                                       30

<210> SEQ ID NO 23
<211> LENGTH: 31
<212> TYPE: DNA
<213> ORGANISM: Artificial
<220> FEATURE:
<223> OTHER INFORMATION: Reverse Primer - Synthetic Construct

<400> SEQUENCE: 23
ccaggtcgac ttagcgaggg ggcagggcct g                                     31

<210> SEQ ID NO 24
<211> LENGTH: 1488
<212> TYPE: DNA
<213> ORGANISM: Artificial
<220> FEATURE:
<223> OTHER INFORMATION: PSCA-CAR -7H - Synthetic Construct

<400> SEQUENCE: 24
gatattcagc tgacccagag cccgagcagc ctgagcgcga gcgtgggcga tcgcgtgacc      60
attacctgca gcgcgagcag cagcgtgcgc tttattcatt ggtatcagca gaaaccgggc     120
aaagcgccga aacgcctgat ttatgatacc agcaaactgg cgagcggcgt gccgagccgc     180
tttagcggca gcggcagcgg caccgatttt accctgacca ttagcagcct gcagccggaa     240
gattttgcga cctattattg ccagcagtgg agcagcagcc cgtttacctt tggccagggc     300
accaaagtgg aaattaaagg cagcaccagc ggcagcggca aacccgggcag cggcgaaggc     360 agcaccaaag gcagcgaagt gcagctggtg gaaagcggcg gcggcctggt gcagccgggc     420
ggcagcctgc gcctgagctg cgcggcgagc ggctttaaca ttaaagatta ttatattcat     480
tgggtgcgcc aggcgccggg caaaggcctg gaatgggtgg cgtggattga tccggaaaac     540
ggcgatagcg aatttgtgcc gaaatttcag ggccgcgcga ccattagcgc ggataccagc     600
aaaaacaccg cgtatctgca gatgaacagc ctgcgcgcgg aagataccgc ggtgtattat     660
tgcaaaaccg cggctttttg gggccagggc accctggtga ccgtgagcag cgcgccgccg     720
cgcgcgagcg cgctgccggc gccgccgacc ggcagcgcgc tgccggatcc gcagaccgcg     780
agcgcgctgc cggatccgcc ggcggcgagc gcgctgccgt ttgggtgctg gtggtggtg     840 ggcggcgtgc tggcgtgcta tagcctgctg gtgaccgtgg cgtttattat tttttgggtg     900
cgcagcaaac gcagcgcgcc tgctgcatagc gattatatga acatgacccc gcgccgcccg     960
ggcccgaccc gcaaacatta tcagccgtat gcgccgccgc gcgattttgc ggcgtatcgc    1020
```

```
agcgtgaaac gcggccgcaa aaaactgctg tatattttta acagccgtt tatgcgcccg    1080 gtgcagacca cccaggaaga agatggctgc agctgccgct ttccggaaga agaagaaggc    1140
ggctgcgaac tgcgcgtgaa atttagccgc agcgcggatg cgccggcgta tcagcagggc    1200
cagaaccagc tgtataacga actgaacctg gccgccgcg aagaatatga tgtgctggat    1260
aaacgccgcg ccgcgatcc ggaaatgggc ggcaaaccgc cgcaaaaa cccgcaggaa    1320 ggcctgtata cgaactgca gaaagataaa atggcgaag cgtatagcga aattggcatg    1380
aaaggcgaac cgccgcgg caaaggccat gatggcctgt atcagggcct gagcaccgcg    1440
accaaagata cctatgatgc gctgcatatg caggcgctgc cgccgcgc                1488

<210> SEQ ID NO 25
<211> LENGTH: 2064
<212> TYPE: DNA
<213> ORGANISM: Artificial
<220> FEATURE:
<223> OTHER INFORMATION: PSCA-CAR -G4HH2H3mt - Synthetic Construct

<400> SEQUENCE: 25
gatattcagc tgacccagag cccgagcagc ctgagcgcga gcgtgggcga tcgcgtgacc      60
attacctgca gcgcgagcag cagcgtgcgc tttattcatt ggtatcagca gaaaccgggc     120
aaagcgccga acgcctgat ttatgatacc agcaaactgg cgagcggcgt gccgagccgc     180
tttagcggca gcggcagcgg caccgatttt accctgacca ttagcagcct gcagccggaa     240
gattttgcga cctattattg ccagcagtgg agcagcagcc cgtttacctt tggccagggc     300
accaaagtgg aaattaaagg cagcaccagc ggcagcggca accgggcag cggcgaaggc     360 agcaccaaag cagcgaagt gcagctggtg aaagcggcg cggcctggt gcagccgggc     420 ggcagcctgc gcctgagctg cgcggcgagc ggctttaaca ttaaagatta ttatattcat     480
tgggtgcgcc aggcgccggg caaaggcctg aatgggtgg cgtggattga tccggaaaac     540 ggcgatacccg aatttgtgcc gaaatttcag ggccgcgcga ccattagcgc ggataccagc     600
aaaaacaccg cgtatctgca gatgaacagc ctgcgcgcgg aagataccgc ggtgtattat     660
tgcaaaaccg gcggctttg gggccagggc accctggtga ccgtgagcag cgaaagcaaa     720
tatggcccgc cgtgcccgcc gtgcccggcg ccgccggtgg cgggcccgag cgtgtttctg     780
tttccgccga accgaaaga tacccctgatg attagccgca ccccgaagt gacctgcgtg     840 gtggtggatg tgagccagga agatccggaa gtgcagttta actggtatgt ggatggcgtg     900
gaagtgcata acgcgaaaac caaaccgcgc gaagaacagt tcagagcac ctatcgcgtg     960 gtgagcgtgc tgaccgtgct gcatcaggat tggctgaacg gcaaagaata taatgcaaa    1020 gtgagcaaca aaggcctgcc gagcagcatt gaaaaaacca ttagcaaagc gaaaggccag    1080
ccgcgcgaac cgcaggtgta ccctgccg ccgagccagg aagaaatgac caaaaaccag    1140
gtgagcctga cctgcctggt gaaaggcttt tatccgagcg atattgcggt ggaatgggaa    1200
agcaacggcc agccggaaaa caactataaa accaccccgc cggtgctgga tagcgatggc    1260
agcttttttc tgtatagccg cctgaccgtg gataaaagcc gctggcagga aggcaacgtg    1320
tttagctgca gcgtgatgca tgaagcgctg cataaccatt atacccagaa aagcctgagc    1380
ctgagcctgg gcaaattttg ggtgctggtg gtggtgggcg gcgtgctggc gtgctatagc    1440
ctgctggtga ccgtggcgtt tattattttt tgggtgcgca gcaaacgcag ccgcctgctg    1500
catagcgatt atatgaacat gacccgcgc cgcccggggcc cgacccgcaa acattatcag    1560
```

```
ccgtatgcgc cgccgcgcga ttttgcggcg tatcgcagcg tgaaacgcgg ccgcaaaaaa   1620
ctgctgtata ttttaaaca gccgtttatg cgcccggtgc agaccaccca ggaagaagat   1680
ggctgcagct gccgctttcc ggaagaagaa gaaggcggct gcgaactgcg cgtgaaattt   1740
agccgcagcg cggatgcgcc ggcgtatcag cagggccaga accagctgta taacgaactg   1800
aacctgggcc gccgcgaaga atatgatgtg ctggataaac gccgcggccg cgatccggaa   1860
atgggcggca aaccgcgccg caaaaacccg caggaaggcc tgtataacga actgcagaaa   1920
gataaaatgg cggaagcgta tagcgaaatt ggcatgaaag cgaacgccg ccgcggcaaa   1980 ggccatgatg gcctgtatca gggcctgagc accgcgacca agataccta tgatgcgctg   2040 catatgcagg cgctgccgcc gcgc                                        2064
```

<210> SEQ ID NO 26
<211> LENGTH: 244
<212> TYPE: PRT
<213> ORGANISM: Artificial
<220> FEATURE:
<223> OTHER INFORMATION: scFV-2 - Synthetic Construct

<400> SEQUENCE: 26

```
Gln Val Lys Leu Gln Glu Ser Gly Gly Gly Leu Val Gln Pro Gly Gly
1               5                   10                  15

Ser Leu Lys Leu Ser Cys Val Ala Ser Gly Phe Thr Phe Ser Ser Tyr
            20                  25                  30

Thr Met Ser Trp Val Arg Arg Thr Pro Glu Lys Arg Leu Glu Trp Val
        35                  40                  45

Ala Tyr Ile His Asn Gly Gly His Thr Tyr Tyr Pro Asp Thr Ile
    50                  55                  60

Lys Gly Arg Phe Thr Ile Ser Arg Asp Asn Ala Lys Asn Thr Leu Phe
65                  70                  75                  80

Leu Glu Met Ser Ser Leu Lys Ser Glu Asp Thr Ala Met Tyr Tyr Cys
                85                  90                  95

Thr Arg Arg Met Tyr Tyr Gly Asn Ser His Trp Tyr Phe Asp Val Trp
            100                 105                 110

Gly Ala Gly Thr Ser Val Thr Val Ser Ser Gly Gly Gly Gly Ser Gly
        115                 120                 125

Gly Gly Gly Ser Gly Gly Gly Ser Asp Ile Gln Met Thr Gln Ser
    130                 135                 140

Pro Ser Ser Leu Ser Ala Ser Val Gly Asp Arg Val Thr Ile Thr Cys
145                 150                 155                 160

Arg Thr Ser Gln Asp Ile Ser Asn Tyr Leu Asn Trp Tyr Gln Gln Lys
                165                 170                 175

Pro Gly Lys Ala Pro Lys Leu Leu Ile Tyr Tyr Thr Leu Lys Leu Asn
            180                 185                 190

Ser Gly Val Pro Ser Arg Phe Ser Gly Ser Gly Ser Gly Thr Asp Phe
        195                 200                 205

Thr Phe Thr Ile Ser Ser Leu Gln Pro Glu Asp Ile Ala Thr Tyr Tyr
    210                 215                 220

Cys Gln Gln Ser Lys Thr Leu Pro Trp Thr Phe Gly Gly Gly Thr Lys
225                 230                 235                 240

Val Glu Ile Lys
```

<210> SEQ ID NO 27
<211> LENGTH: 233
<212> TYPE: PRT

<213> ORGANISM: Artificial
<220> FEATURE:
<223> OTHER INFORMATION: scFV-3 - Synthetic Construct

<400> SEQUENCE: 27

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Tyr
            20                  25                  30

Tyr Ile His Trp Val Arg Gln Ala Pro Gly Lys Gly Leu Glu Trp Val
        35                  40                  45

Ala Trp Ile Asp Pro Glu Asn Gly Asp Thr Glu Phe Val Pro Lys Phe
    50                  55                  60

Gln Gly Arg Ala Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Lys Thr Gly Gly Phe Trp Gly Gln Gly Thr Leu Val Thr Val Ser Ser
            100                 105                 110

Gly Gly Gly Gly Ser Gly Gly Gly Ser Gly Gly Gly Gly Ser Asp
        115                 120                 125

Ile Gln Leu Thr Gln Ser Pro Ser Ser Leu Ser Ala Ser Val Gly Asp
    130                 135                 140

Arg Val Thr Ile Thr Cys Ser Ala Ser Ser Val Arg Phe Ile His
145                 150                 155                 160

Trp Tyr Gln Gln Lys Pro Gly Lys Ala Pro Lys Arg Leu Ile Tyr Asp
                165                 170                 175

Thr Ser Lys Leu Ala Ser Gly Val Pro Ser Arg Phe Ser Gly Ser Gly
            180                 185                 190

Ser Gly Thr Asp Phe Thr Leu Thr Ile Ser Ser Leu Gln Pro Glu Asp
        195                 200                 205

Phe Ala Thr Tyr Tyr Cys Gln Gln Trp Ser Ser Pro Phe Thr Phe
    210                 215                 220

Gly Gln Gly Thr Lys Val Glu Ile Lys
225                 230
```

<210> SEQ ID NO 28
<211> LENGTH: 505
<212> TYPE: PRT
<213> ORGANISM: Artificial
<220> FEATURE:
<223> OTHER INFORMATION: PSCA-CAR-8H(dc) - Synthetic Construct

<400> SEQUENCE: 28

```
Asp Ile Gln Leu Thr Gln Ser Pro Ser Ser Leu Ser Ala Ser Val Gly
1               5                   10                  15

Asp Arg Val Thr Ile Thr Cys Ser Ala Ser Ser Val Arg Phe Ile
            20                  25                  30

His Trp Tyr Gln Gln Lys Pro Gly Lys Ala Pro Lys Arg Leu Ile Tyr
        35                  40                  45

Asp Thr Ser Lys Leu Ala Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Ser Ser Pro Phe Thr
                85                  90                  95
```

```
Phe Gly Gln Gly Thr Lys Val Glu Ile Lys Gly Ser Thr Ser Gly Ser
                100                 105                 110
Gly Lys Pro Gly Ser Gly Glu Gly Ser Thr Lys Gly Ser Glu Val Gln
            115                 120                 125
Leu Val Glu Ser Gly Gly Gly Leu Val Gln Pro Gly Gly Ser Leu Arg
        130                 135                 140
Leu Ser Cys Ala Ala Ser Gly Phe Asn Ile Lys Asp Tyr Tyr Ile His
145                 150                 155                 160
Trp Val Arg Gln Ala Pro Gly Lys Gly Leu Glu Trp Val Ala Trp Ile
                165                 170                 175
Asp Pro Glu Asn Gly Asp Thr Glu Phe Val Pro Lys Phe Gln Gly Arg
            180                 185                 190
Ala Thr Ile Ser Ala Asp Thr Ser Lys Asn Thr Ala Tyr Leu Gln Met
        195                 200                 205
Asn Ser Leu Arg Ala Glu Asp Thr Ala Val Tyr Tyr Cys Lys Thr Gly
        210                 215                 220
Gly Phe Trp Gly Gln Gly Thr Leu Val Thr Val Ser Ser Lys Pro Thr
225                 230                 235                 240
Thr Thr Pro Ala Pro Arg Pro Pro Thr Pro Ala Pro Thr Ile Ala Ser
                245                 250                 255
Gln Pro Leu Ser Leu Arg Pro Glu Ala Arg Pro Ala Ala Gly Gly Ala
            260                 265                 270
Val His Thr Arg Gly Leu Asp Phe Ala Asp Phe Trp Val Leu Val Val
        275                 280                 285
Val Gly Gly Val Leu Ala Cys Tyr Ser Leu Leu Val Thr Val Ala Phe
        290                 295                 300
Ile Ile Phe Trp Val Arg Ser Lys Arg Ser Arg Leu Leu His Ser Asp
305                 310                 315                 320
Tyr Met Asn Met Thr Pro Arg Arg Pro Gly Pro Thr Arg Lys His Tyr
                325                 330                 335
Gln Pro Tyr Ala Pro Pro Arg Asp Phe Ala Ala Tyr Arg Ser Val Lys
            340                 345                 350
Arg Gly Arg Lys Lys Leu Leu Tyr Ile Phe Lys Gln Pro Phe Met Arg
        355                 360                 365
Pro Val Gln Thr Thr Gln Glu Glu Asp Gly Cys Ser Cys Arg Phe Pro
370                 375                 380
Glu Glu Glu Glu Gly Gly Cys Glu Leu Arg Val Lys Phe Ser Arg Ser
385                 390                 395                 400
Ala Asp Ala Pro Ala Tyr Gln Gln Gly Gln Asn Gln Leu Tyr Asn Glu
                405                 410                 415
Leu Asn Leu Gly Arg Arg Glu Glu Tyr Asp Val Leu Asp Lys Arg Arg
            420                 425                 430
Gly Arg Asp Pro Glu Met Gly Gly Lys Pro Arg Arg Lys Asn Pro Gln
        435                 440                 445
Glu Gly Leu Tyr Asn Glu Leu Gln Lys Asp Lys Met Ala Glu Ala Tyr
        450                 455                 460
Ser Glu Ile Gly Met Lys Gly Glu Arg Arg Arg Gly Lys Gly His Asp
465                 470                 475                 480
Gly Leu Tyr Gln Gly Leu Ser Thr Ala Thr Lys Asp Thr Tyr Asp Ala
                485                 490                 495
Leu His Met Gln Ala Leu Pro Pro Arg
            500                 505
```

<210> SEQ ID NO 29
<211> LENGTH: 461
<212> TYPE: PRT
<213> ORGANISM: Artificial
<220> FEATURE:
<223> OTHER INFORMATION: PSCA-CAR1 - Synthetic Construct

<400> SEQUENCE: 29

```
Asp Ile Gln Leu Thr Gln Ser Pro Ser Ser Leu Ser Ala Ser Val Gly
1               5                   10                  15

Asp Arg Val Thr Ile Thr Cys Ser Ala Ser Ser Val Arg Phe Ile
            20                  25                  30

His Trp Tyr Gln Gln Lys Pro Gly Lys Ala Pro Lys Arg Leu Ile Tyr
        35                  40                  45

Asp Thr Ser Lys Leu Ala Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Ser Ser Pro Phe Thr
                85                  90                  95

Phe Gly Gln Gly Thr Lys Val Glu Ile Lys Gly Ser Thr Ser Gly Ser
            100                 105                 110

Gly Lys Pro Gly Ser Gly Glu Gly Ser Thr Lys Gly Ser Glu Val Gln
        115                 120                 125

Leu Val Glu Ser Gly Gly Gly Leu Val Gln Pro Gly Gly Ser Leu Arg
130                 135                 140

Leu Ser Cys Ala Ala Ser Gly Phe Asn Ile Lys Asp Tyr Tyr Ile His
145                 150                 155                 160

Trp Val Arg Gln Ala Pro Gly Lys Gly Leu Glu Trp Val Ala Trp Ile
                165                 170                 175

Asp Pro Glu Asn Gly Asp Thr Glu Phe Val Pro Lys Phe Gln Gly Arg
            180                 185                 190

Ala Thr Ile Ser Ala Asp Thr Ser Lys Asn Thr Ala Tyr Leu Gln Met
        195                 200                 205

Asn Ser Leu Arg Ala Glu Asp Thr Ala Val Tyr Tyr Cys Lys Thr Gly
210                 215                 220

Gly Phe Trp Gly Gln Gly Thr Leu Val Thr Val Ser Ser Lys Pro Thr
225                 230                 235                 240

Thr Thr Pro Ala Pro Arg Pro Pro Thr Pro Ala Pro Thr Ile Ala Ser
                245                 250                 255

Gln Pro Leu Ser Leu Arg Pro Glu Ala Arg Pro Ala Ala Gly Gly Ala
            260                 265                 270

Val His Thr Arg Gly Leu Asp Phe Ala Asp Ile Tyr Ile Trp Ala Pro
        275                 280                 285

Leu Ala Gly Thr Cys Gly Val Leu Leu Leu Ser Leu Val Ile Thr Leu
290                 295                 300

Tyr Cys Val Lys Arg Gly Arg Lys Lys Leu Leu Tyr Ile Phe Lys Gln
305                 310                 315                 320

Pro Phe Met Arg Pro Val Gln Thr Thr Gln Glu Glu Asp Gly Cys Ser
                325                 330                 335

Cys Arg Phe Pro Glu Glu Glu Glu Gly Gly Cys Glu Leu Arg Val Lys
            340                 345                 350

Phe Ser Arg Ser Ala Asp Ala Pro Ala Tyr Gln Gln Gly Gln Asn Gln
        355                 360                 365

Leu Tyr Asn Glu Leu Asn Leu Gly Arg Arg Glu Glu Tyr Asp Val Leu
```

```
            370                 375                 380
Asp Lys Arg Arg Gly Arg Asp Pro Glu Met Gly Gly Lys Pro Arg Arg
385                 390                 395                 400

Lys Asn Pro Gln Glu Gly Leu Tyr Asn Glu Leu Gln Lys Asp Lys Met
                405                 410                 415

Ala Glu Ala Tyr Ser Glu Ile Gly Met Lys Gly Glu Arg Arg Arg Gly
                420                 425                 430

Lys Gly His Asp Gly Leu Tyr Gln Gly Leu Ser Thr Ala Thr Lys Asp
                435                 440                 445

Thr Tyr Asp Ala Leu His Met Gln Ala Leu Pro Pro Arg
            450                 455                 460

<210> SEQ ID NO 30
<211> LENGTH: 461
<212> TYPE: PRT
<213> ORGANISM: Artificial
<220> FEATURE:
<223> OTHER INFORMATION: PSCA-CAR2 - Synthetic Construct

<400> SEQUENCE: 30

Asp Ile Gln Leu Thr Gln Ser Pro Ser Ser Leu Ser Ala Ser Val Gly
1               5                   10                  15

Asp Arg Val Thr Ile Thr Cys Ser Ala Ser Ser Ser Val Arg Phe Ile
            20                  25                  30

His Trp Tyr Gln Gln Lys Pro Gly Lys Ala Pro Lys Arg Leu Ile Tyr
        35                  40                  45

Asp Thr Ser Lys Leu Ala Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Ser Ser Ser Pro Phe Thr
                85                  90                  95

Phe Gly Gln Gly Thr Lys Val Glu Ile Lys Gly Ser Thr Ser Gly Ser
            100                 105                 110

Gly Lys Pro Gly Ser Gly Glu Gly Ser Thr Lys Gly Ser Glu Val Gln
        115                 120                 125

Leu Val Glu Ser Gly Gly Gly Leu Val Gln Pro Gly Gly Ser Leu Arg
    130                 135                 140

Leu Ser Cys Ala Ala Ser Gly Phe Asn Ile Lys Asp Tyr Tyr Ile His
145                 150                 155                 160

Trp Val Arg Gln Ala Pro Gly Lys Gly Leu Glu Trp Val Ala Trp Ile
                165                 170                 175

Asp Pro Glu Asn Gly Asp Thr Glu Phe Val Pro Lys Phe Gln Gly Arg
            180                 185                 190

Ala Thr Ile Ser Ala Asp Thr Ser Lys Asn Thr Ala Tyr Leu Gln Met
        195                 200                 205

Asn Ser Leu Arg Ala Glu Asp Thr Ala Val Tyr Tyr Cys Lys Thr Gly
    210                 215                 220

Gly Phe Trp Gly Gln Gly Thr Leu Val Thr Val Ser Ser Lys Pro Thr
225                 230                 235                 240

Thr Thr Pro Ala Pro Arg Pro Pro Thr Pro Ala Pro Thr Ile Ala Ser
                245                 250                 255

Gln Pro Leu Ser Leu Arg Pro Glu Ala Arg Pro Ala Ala Gly Gly Ala
            260                 265                 270

Val His Thr Arg Gly Leu Asp Phe Ala Asp Phe Trp Val Leu Val Val
```

|  |  |  | 275 |  |  |  | 280 |  |  |  | 285 |  |  |
|--|--|--|--|--|--|--|--|--|--|--|--|--|--|
| Val | Gly | Gly | Val | Leu | Ala | Cys | Tyr | Ser | Leu | Leu | Val | Thr | Val | Ala | Phe |
|  |  |  | 290 |  |  |  | 295 |  |  |  | 300 |  |  |

Ile Ile Phe Trp Val Arg Ser Lys Arg Ser Arg Leu Leu His Ser Asp
305                 310                 315                 320

Tyr Met Asn Met Thr Pro Arg Arg Pro Gly Pro Thr Arg Lys His Tyr
                325                 330                 335

Gln Pro Tyr Ala Pro Pro Arg Asp Phe Ala Ala Tyr Arg Ser Val Lys
                340                 345                 350

Phe Ser Arg Ser Ala Asp Ala Pro Ala Tyr Gln Gln Gly Gln Asn Gln
                355                 360                 365

Leu Tyr Asn Glu Leu Asn Leu Gly Arg Arg Glu Glu Tyr Asp Val Leu
                370                 375                 380

Asp Lys Arg Arg Gly Arg Asp Pro Glu Met Gly Gly Lys Pro Arg Arg
385                 390                 395                 400

Lys Asn Pro Gln Glu Gly Leu Tyr Asn Glu Leu Gln Lys Asp Lys Met
                405                 410                 415

Ala Glu Ala Tyr Ser Glu Ile Gly Met Lys Gly Glu Arg Arg Arg Gly
                420                 425                 430

Lys Gly His Asp Gly Leu Tyr Gln Gly Leu Ser Thr Ala Thr Lys Asp
                435                 440                 445

Thr Tyr Asp Ala Leu His Met Gln Ala Leu Pro Pro Arg
450                 455                 460

<210> SEQ ID NO 31
<211> LENGTH: 1515
<212> TYPE: DNA
<213> ORGANISM: Artificial
<220> FEATURE:
<223> OTHER INFORMATION: PSCA-CAR -8H(dc) - Synthetic Construct

<400> SEQUENCE: 31

```
gatattcagc tgacccagag cccgagcagc ctgagcgcga gcgtgggcga tcgcgtgacc      60
attacctgca gcgcgagcag cagcgtgcgc tttattcatt ggtatcagca gaaaccgggc     120
aaagcgccga aacgcctgat ttatgatacc agcaaactgg cgagcggcgt gccgagccgc     180
tttagcggca gcggcagcgg caccgatttt accctgacca ttagcagcct gcagccggaa     240
gattttgcga cctattattg ccagcagtgg agcagcagcc gtttaccttt ggccagggc      300
accaaagtgg aaattaaagg cagcaccagc ggcagcggca aaccgggcag cggcgaaggc     360
agcaccaaag cagcgaagt gcagctggtg gaaagcggcg cggcctggt gcagccgggc       420
ggcagcctgc gcctgagctg cgcggcgagc ggctttaaca ttaaagatta ttatattcat     480
tgggtgcgcc aggcgccggg caaaggcctg aatgggtgg cgtggattga tccggaaaac     540
ggcgataccg aatttgtgcc gaaatttcag ggccgcgcga ccattagcgc ggataccagc     600
aaaaacaccg cgtatctgca gatgaacagc ctgcgcgcgg aagataccgc ggtgtattat     660
tgcaaaaccg gcggctttg gggccagggc accctggtga ccgtgagcag caaaccgacc     720
accaccccgg cgccgcgccc gccgaccccg gcgccgacca ttgcgagcca gccgctgagc     780
ctgcgcccgg aagcgcgccc ggcggcgggc ggcgcggtgc ataccgcgg cctggatttt     840
gcggattttt gggtgctggt ggtggtgggc ggcgtgctgg cgtgctatag cctgctggtg     900
accgtggcgt ttattatttt ttgggtgcgc agcaaacgca gccgcctgct gcatagcgat     960
tatatgaaca tgacccccgcg ccgccgggc ccgacccgca acattatca gccgtatgcg    1020
```

```
ccgccgcgcg attttgcggc gtatcgcagc gtgaaacgcg gccgcaaaaa actgctgtat    1080
atttttaaac agccgtttat gcgcccggtg cagaccaccc aggaagaaga tggctgcagc    1140
tgccgctttc cggaagaaga agaaggcggc tgcgaactgc gcgtgaaatt tagccgcagc    1200
gcggatgcgc cggcgtatca gcagggccag aaccagctgt ataacgaact gaacctgggc    1260
cgccgcgaag aatatgatgt gctggataaa cgccgcggcc gcgatccgga aatgggcggc    1320
aaaccgcgcc gcaaaaaccc gcaggaaggc ctgtataacg aactgcagaa agataaaatg    1380
gcggaagcgt atagcgaaat tggcatgaaa ggcgaacgcc gccgcggcaa aggccatgat    1440
ggcctgtatc agggcctgag caccgcgacc aaagatacct atgatgcgct gcatatgcag    1500
gcgctgccgc cgcgc                                                     1515
```

<210> SEQ ID NO 32
<211> LENGTH: 135
<212> TYPE: DNA
<213> ORGANISM: Artificial
<220> FEATURE:
<223> OTHER INFORMATION: 8H(dc) - Synthetic Construct

<400> SEQUENCE: 32

```
aaaccgacca ccaccccggc gccgcgcccg ccgaccccgg cgccgaccat tgcgagccag     60
ccgctgagcc tgcgcccgga agcgcgcccg gcggcgggcg gcgcggtgca tacccgcggc    120
ctggattttg cggat                                                    135
```

<210> SEQ ID NO 33
<211> LENGTH: 12
<212> TYPE: PRT
<213> ORGANISM: Artificial
<220> FEATURE:
<223> OTHER INFORMATION: G4Hinge - Synthetic Construct

<400> SEQUENCE: 33

Glu Ser Lys Tyr Gly Pro Pro Cys Pro Pro Cys Pro
1               5                   10

<210> SEQ ID NO 34
<211> LENGTH: 119
<212> TYPE: PRT
<213> ORGANISM: Artificial
<220> FEATURE:
<223> OTHER INFORMATION: G4HH3 - Synthetic Construct

<400> SEQUENCE: 34

Glu Ser Lys Tyr Gly Pro Pro Cys Pro Pro Cys Pro Gly Gln Pro Arg
1               5                   10                  15

Glu Pro Gln Val Tyr Thr Leu Pro Pro Ser Gln Glu Glu Met Thr Lys
            20                  25                  30

Asn Gln Val Ser Leu Thr Cys Leu Val Lys Gly Phe Tyr Pro Ser Asp
        35                  40                  45

Ile Ala Val Glu Trp Glu Ser Asn Gly Gln Pro Glu Asn Asn Tyr Lys
    50                  55                  60

Thr Thr Pro Pro Val Leu Asp Ser Asp Gly Ser Phe Phe Leu Tyr Ser
65                  70                  75                  80

Arg Leu Thr Val Asp Lys Ser Arg Trp Gln Glu Gly Asn Val Phe Ser
                85                  90                  95

Cys Ser Val Met His Glu Ala Leu His Asn His Tyr Thr Gln Lys Ser
            100                 105                 110

Leu Ser Leu Ser Leu Gly Lys
        115

```
<210> SEQ ID NO 35
<211> LENGTH: 24
<212> TYPE: DNA
<213> ORGANISM: Artificial
<220> FEATURE:
<223> OTHER INFORMATION: BBZ-HF - Synthetic Construct

<400> SEQUENCE: 35
cagaagaaga agaaggagga tgtg                                          24

<210> SEQ ID NO 36
<211> LENGTH: 24
<212> TYPE: DNA
<213> ORGANISM: Artificial
<220> FEATURE:
<223> OTHER INFORMATION: BBZ-HR - Synthetic Construct

<400> SEQUENCE: 36
tactcctctc ttcgtcctag attg                                          24

<210> SEQ ID NO 37
<211> LENGTH: 470
<212> TYPE: PRT
<213> ORGANISM: Artificial
<220> FEATURE:
<223> OTHER INFORMATION: Synthetic Construct

<400> SEQUENCE: 37
```

Asp Ile Gln Met Thr Gln Ser Pro Ser Ser Leu Ser Ala Ser Val Gly
1               5                   10                  15

Asp Arg Val Thr Ile Thr Cys Arg Thr Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Leu Lys Leu Asn Ser Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Ser Lys Thr Leu Pro Trp
                85                  90                  95

Thr Phe Gly Gly Gly Thr Lys Val Glu Ile Lys Gly Ser Thr Ser Gly
            100                 105                 110

Ser Gly Lys Pro Gly Ser Gly Glu Gly Ser Thr Lys Gly Gln Val Lys
        115                 120                 125

Leu Gln Glu Ser Gly Gly Gly Leu Val Gln Pro Gly Gly Ser Leu Lys
    130                 135                 140

Leu Ser Cys Val Ala Ser Gly Phe Thr Phe Ser Ser Tyr Thr Met Ser
145                 150                 155                 160

Trp Val Arg Arg Thr Pro Glu Lys Arg Leu Glu Trp Val Ala Tyr Ile
                165                 170                 175

His Asn Gly Gly Gly His Thr Tyr Tyr Pro Asp Thr Ile Lys Gly Arg
            180                 185                 190

Phe Thr Ile Ser Arg Asp Asn Ala Lys Asn Thr Leu Phe Leu Glu Met
        195                 200                 205

Ser Ser Leu Lys Ser Glu Asp Thr Ala Met Tyr Tyr Cys Thr Arg Arg
    210                 215                 220

Met Tyr Tyr Gly Asn Ser His Trp Tyr Phe Asp Val Trp Gly Ala Gly

```
                 225                 230                 235                 240
        Thr Ser Val Thr Val Ser Lys Pro Thr Thr Thr Pro Ala Pro Arg Pro
                         245                 250                 255

Pro Thr Pro Ala Pro Thr Ile Ala Ser Gln Pro Leu Ser Leu Arg Pro
                         260                 265                 270

Glu Ala Arg Pro Ala Ala Gly Gly Ala Val His Thr Arg Gly Leu Asp
                         275                 280                 285

Phe Ala Asp Ile Tyr Ile Trp Ala Pro Leu Ala Gly Thr Cys Gly Val
                         290                 295                 300

Leu Leu Leu Ser Leu Val Ile Thr Leu Tyr Cys Val Lys Arg Gly Arg
        305                 310                 315                 320

Lys Lys Leu Leu Tyr Ile Phe Lys Gln Pro Phe Met Arg Pro Val Gln
                         325                 330                 335

Thr Thr Gln Glu Glu Asp Gly Cys Ser Cys Arg Phe Pro Glu Glu Glu
                         340                 345                 350

Glu Gly Gly Cys Glu Leu Arg Val Lys Phe Ser Arg Ser Ala Asp Ala
                         355                 360                 365

Pro Ala Tyr Gln Gln Gly Gln Asn Gln Leu Tyr Asn Glu Leu Asn Leu
                         370                 375                 380

Gly Arg Arg Glu Glu Tyr Asp Val Leu Asp Lys Arg Arg Gly Arg Asp
        385                 390                 395                 400

Pro Glu Met Gly Gly Lys Pro Arg Arg Lys Asn Pro Gln Glu Gly Leu
                         405                 410                 415

Tyr Asn Glu Leu Gln Lys Asp Lys Met Ala Glu Ala Tyr Ser Glu Ile
                         420                 425                 430

Gly Met Lys Gly Glu Arg Arg Arg Gly Lys Gly His Asp Gly Leu Tyr
                         435                 440                 445

Gln Gly Leu Ser Thr Ala Thr Lys Asp Thr Tyr Asp Ala Leu His Met
                         450                 455                 460

Gln Ala Leu Pro Pro Arg
        465                 470

<210> SEQ ID NO 38
<211> LENGTH: 318
<212> TYPE: PRT
<213> ORGANISM: Artificial
<220> FEATURE:
<223> OTHER INFORMATION: Synthetic Construct

<400> SEQUENCE: 38

Asp Ile Gln Met Thr Gln Ser Pro Ser Ser Leu Ser Ala Ser Val Gly
        1               5                   10                  15

Asp Arg Val Thr Ile Thr Cys Arg Thr Ser Gln Asp Ile Ser Asn Tyr
                        20                  25                  30

Leu Asn Trp Tyr Gln Gln Lys Pro Gly Lys Ala Pro Lys Leu Leu Ile
                    35                  40                  45

Tyr Tyr Thr Leu Lys Leu Asn Ser Gly Val Pro Ser Arg Phe Ser Gly
            50                  55                  60

Ser Gly Ser Gly Thr Asp Phe Thr Phe Thr Ile Ser Ser Leu Gln Pro
        65                  70                  75                  80

Glu Asp Ile Ala Thr Tyr Tyr Cys Gln Gln Ser Lys Thr Leu Pro Trp
                        85                  90                  95

Thr Phe Gly Gly Gly Thr Lys Val Glu Ile Lys Gly Ser Thr Ser Gly
                    100                 105                 110

Ser Gly Lys Pro Gly Ser Gly Glu Gly Ser Thr Lys Gly Gln Val Lys
```

```
                    115                 120                 125
Leu Gln Glu Ser Gly Gly Gly Leu Val Gln Pro Gly Gly Ser Leu Lys
    130                 135                 140

Leu Ser Cys Val Ala Ser Gly Phe Thr Phe Ser Ser Tyr Thr Met Ser
145                 150                 155                 160

Trp Val Arg Arg Thr Pro Glu Lys Arg Leu Glu Trp Val Ala Tyr Ile
                165                 170                 175

His Asn Gly Gly Gly His Thr Tyr Tyr Pro Asp Thr Ile Lys Gly Arg
            180                 185                 190

Phe Thr Ile Ser Arg Asp Asn Ala Lys Asn Thr Leu Phe Leu Glu Met
        195                 200                 205

Ser Ser Leu Lys Ser Glu Asp Thr Ala Met Tyr Tyr Cys Thr Arg Arg
210                 215                 220

Met Tyr Tyr Gly Asn Ser His Trp Tyr Phe Asp Val Trp Gly Ala Gly
225                 230                 235                 240

Thr Ser Val Thr Val Ser Lys Pro Thr Thr Thr Pro Ala Pro Arg Pro
                245                 250                 255

Pro Thr Pro Ala Pro Thr Ile Ala Ser Gln Pro Leu Ser Leu Arg Pro
            260                 265                 270

Glu Ala Arg Pro Ala Ala Gly Gly Ala Val His Thr Arg Gly Leu Asp
        275                 280                 285

Phe Ala Asp Phe Trp Val Leu Val Val Val Gly Val Leu Ala Cys
290                 295                 300

Tyr Ser Leu Leu Val Thr Val Ala Phe Ile Ile Phe Trp Val
305                 310                 315

<210> SEQ ID NO 39
<211> LENGTH: 234
<212> TYPE: PRT
<213> ORGANISM: Artificial
<220> FEATURE:
<223> OTHER INFORMATION: Synthetic Construct

<400> SEQUENCE: 39

Asp Ile Gln Leu Thr Gln Ser Pro Ser Ser Leu Ser Ala Ser Val Gly
1               5                   10                  15

Asp Arg Val Thr Ile Thr Cys Ser Ala Ser Ser Ser Val Arg Phe Ile
            20                  25                  30

His Trp Tyr Gln Gln Lys Pro Gly Lys Ala Pro Lys Arg Leu Ile Tyr
        35                  40                  45

Asp Thr Ser Lys Leu Ala Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Ser Ser Ser Pro Phe Thr
                85                  90                  95

Phe Gly Gln Gly Thr Lys Val Glu Ile Lys Gly Gly Gly Gly Ser Gly
            100                 105                 110

Gly Gly Gly Ser Gly Gly Gly Gly Ser Ser Glu Val Gln Leu Val Glu
        115                 120                 125

Ser Gly Gly Gly Leu Val Gln Pro Gly Gly Ser Leu Arg Leu Ser Cys
    130                 135                 140

Ala Ala Ser Gly Phe Asn Ile Lys Asp Tyr Tyr Ile His Trp Val Arg
145                 150                 155                 160

Gln Ala Pro Gly Lys Gly Leu Glu Trp Val Ala Trp Ile Asp Pro Glu
```

```
                 165                 170                 175
Asn Gly Asp Thr Glu Phe Val Pro Lys Phe Gln Gly Arg Ala Thr Ile
            180                 185                 190

Ser Ala Asp Thr Ser Lys Asn Thr Ala Tyr Leu Gln Met Asn Ser Leu
        195                 200                 205

Arg Ala Glu Asp Thr Ala Val Tyr Tyr Cys Lys Thr Gly Gly Phe Trp
    210                 215                 220

Gly Gln Gly Thr Leu Val Thr Val Ser Ser
225                 230

<210> SEQ ID NO 40
<211> LENGTH: 236
<212> TYPE: PRT
<213> ORGANISM: Artificial
<220> FEATURE:
<223> OTHER INFORMATION: Synthetic Construct

<400> SEQUENCE: 40

Asp Ile Gln Leu Thr Gln Ser Pro Ser Ser Leu Ser Ala Ser Val Gly
1               5                   10                  15

Asp Arg Val Thr Ile Thr Cys Ser Ala Ser Ser Ser Val Arg Phe Ile
            20                  25                  30

His Trp Tyr Gln Gln Lys Pro Gly Lys Ala Pro Lys Arg Leu Ile Tyr
        35                  40                  45

Asp Thr Ser Lys Leu Ala Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Ser Ser Ser Pro Phe Thr
            85                  90                  95

Phe Gly Gln Gly Thr Lys Val Glu Ile Lys Gly Ser Thr Ser Gly Ser
        100                 105                 110

Gly Lys Pro Gly Ser Gly Glu Gly Ser Thr Lys Gly Glu Val Gln Leu
    115                 120                 125

Val Glu Ser Gly Gly Gly Leu Val Gln Pro Gly Gly Ser Leu Arg Leu
130                 135                 140

Ser Cys Ala Ala Ser Gly Phe Asn Ile Lys Asp Tyr Tyr Ile His Trp
145                 150                 155                 160

Val Arg Gln Ala Pro Gly Lys Gly Leu Glu Trp Val Ala Trp Ile Asp
            165                 170                 175

Pro Glu Asn Gly Asp Thr Glu Phe Val Pro Lys Phe Gln Gly Arg Ala
        180                 185                 190

Thr Ile Ser Ala Asp Thr Ser Lys Asn Thr Ala Tyr Leu Gln Met Asn
    195                 200                 205

Ser Leu Arg Ala Glu Asp Thr Ala Val Tyr Tyr Cys Lys Thr Gly Gly
210                 215                 220

Phe Trp Gly Gln Gly Thr Leu Val Thr Val Ser Ser
225                 230                 235
```

HINGE AREA AND USE OF SAME IN CONSTRUCTING CAR SKELETON

FIELD OF INVENTION

The present invention belongs to immunotherapy field, relating to an improved hinge region and use of same in constructing CAR skeleton, specifically relating to a hinge region which can prolong the survival of CAR-T cells in vivo and/or improve the capability of CAR-T cells to infiltrate tumors and use of same in constructing CAR skeleton.

SEQUENCE LISTING

A sequence listing under 37 CFR 1.821 as an ASCII text file is submitted herewith, the content of which is incorporated by reference in its entirety. The ASCII text file is entitled "EZI1PN001JGC_amended_clean_sequence_listing_ST25.txt" with a date of creation of Dec. 28, 2023 and a size of 81,408 bytes. No new matter is added by way of the present amendments to the specification and the submission of the sequence listing.

BACKGROUND OF THE INVENTION

Chimeric antigen receptor (CAR) is an artificial receptor that mimics TCR function, including antigen recognition region, hinge region, transmembrane region and intracellular signal region. The intracellular signal region is commonly CD3ζ chain or FcRγ, or connected with one or more costimulatory molecules, such as 4-1BB (CD137), CD28, ICOS (CD278). When the antigen (receptor) on the surface of tumor cells is combined with the antibody (ligand) of chimeric antigen receptor, a signal is transmitted into cells through the hinge region and transmembrane region, and the signal region in cells converts the signal into activation signal, which activates effector cells, and the effector cells proliferate and produce cytokines to kill tumor cells.

In recent years, chimeric antigen receptor T lymphocyte (CAR-T) shows significant therapeutic effect on tumor treatment, especially in the treatment of CD19 positive malignant tumors. However, even for acute lymphoblastic leukemia (ALL) with significant therapeutic effect, the median CR (complete remission) time is generally about 8 months after treatment, a large number of patients relapse afterwards, which may be related to the short survival time of CAR-T cells in patients. Therefore, it is of great significance to prolong the survival time of CAR-T in vivo for the CAR-T therapeutic effect.

Although more and more attention has been directed to the study of solid tumor with CAR-T, but most of the CAR-T treatments of solid tumors are not satisfactory. On one hand, CAR-T cells have short survival time in vivo, and the rapid death of CAR-T cells affects the effectiveness of killing. On the other hand, most solid tumors are multipotent in metabolism, immune escape, and tissue formation, limiting the capability of the immune system to control and kill them in many ways. As a result, it is difficult for CAR-T cells to infiltrate into the tumor tissues of solid tumors, accordingly CAR-T therapy has little effect on large solid tumor. To prolong the survival of CAR-T in vivo and to promote the infiltration of CAR-T cells in solid tumor tissues can effectively kill the tumor and inhibit the recurrence of tumor cells, but at the moment there is still no effective way to prolong the in vivo survival of CAR-T as well as to promote the tumor infiltration of CAR-T cells.

SUMMARY OF THE INVENTION

In view of this, one object of the present invention is to provide a hinge region capable of prolonging survival time of CAR-T cells in vivo and/or improving the capability of CAR-T cells to infiltrate tumors. The CAR-T containing the hinge region of the invention has longer survival time in vivo, the capability of cells to infiltrate tumors is significantly enhanced, and the killing effect is better.

To achieve the above objectives, the technical solution of the present invention comprises:

A hinge region for prolonging survival time of CAR-T cells in vivo and/or improving the capability of the CAR-T cells to infiltrate a tumor, wherein the hinge region is provided in the amino acid sequence as shown in SEQ ID NO: 1 or SEQ ID NO:2 or SEQ ID NO:3.

Furthermore, the hinge region is provided in the amino acid sequence as shown in SEQ ID NO:20 or SEQ ID NO:21 or SEQ ID NO:32.

When the antigen (receptor) on the surface of tumor cells is combined with the antibody (ligand) of chimeric antigen receptor, a signal is transmitted into cells through the hinge region and transmembrane region, and the signal region in cells converts the signal into activation signal, which activates effector cells, and the effector cells proliferate and produce cytokines to kill tumor cells. Through the research of reconstruction of the CAR hinge region structure, the applicant found that the structure of the hinge region is closely related to the survival of CAR-T in vivo and the capability of tumor infiltration.

The hinge region is also called spacer or hinge, connecting the CAR antigen recognition region and the transmembrane region. The hinge region should be flexible enough to allow the antigen-binding region to be oriented in different directions to promote antigen recognition. Hinges of different lengths play different roles in the stability of CAR-T. Through a variety of combinations, the applicant unexpectedly discovered that the hinge region has an important influence on survival of CAR-T in vivo and tumor infiltration, and the applicant finally obtained a hinge sequence that can effectively prolong the survival of CAR-T in vivo and promote CAR-T cell tumor infiltration through a lot of screening work, the hinge sequence is provided in SEQ ID NO:1 or SEQ ID NO:2 or SEQ ID NO:3 and is named 7H or G4HH2H3mt or 8H (dc).

The inventor designed 6 hinge structures in total: 8H (dc), 7H, G4Hinge, G4HH3, G4HH2H3mt and DH, of which the amino acid sequences of 7H, G4HH2H3mt and 8H (dc) are shown as SEQ ID NO:1, SEQ ID NO:2 and SEQ ID NO:3, and the nucleotide sequences are shown as SEQ ID NO:20, SEQ ID NO:21 and SEQ ID NO:32. The amino acid sequences of G4Hinge, G4HH3 and G4HH2H3mt are listed in Table 1.

Through the comparison of the CAR-T cell CAR positive rate, CAR-T killing effect in vivo and in vitro, and survival of CAR-T in vivo and/or CAR-T cell tumor infiltration of the currently commonly used hinge structure G4h (G4HH2H3) and 8H separately, it was found that the CAR-T cells with CAR hinge structure of 8H (dc) or 7H or G4HH2H3mt survived longer in vivo, and the CAR-T cells with 7H, G4HH2H3mt and 8H (dc) showed significantly enhanced tumor infiltration capability and had better killing effect compared with CAR-T with G4HH2H3 or 8H hinges.

The amino acid sequence of G4HH2H3 (SEQ ID NO: 4) is listed below:

ESKYGPPCPPCPAPEFLGGPSVFLFPPKPKDTLMISRTPEVTCVVVDVSQ
EDPEVQFNWYVDGVEVHNAKTKPREEQFNSTYRVVSVLTVLHQDWLNGKE
YKCKVSNKGLPSSIEKTISKAKGQPREPQVYTLPPSQEEMTKNQVSLTCL
VKGFYPSDIAVEWESNGQPENNYKTTPPVLDSDGSFFLYSRLTVDKSRWQ
EGNVFSCSVMHEALHNHYTQKSLSLSLGK

The amino acid sequence of 8H (SEQ ID NO:5) is listed below:

KPTTTPAPRPPTPAPTIASQPLSLRPEACRPAAGGAVHTRGLDFACD

A modification method of hinge for prolonging the survival of CAR-T cells in vivo and/or improving the capability of CAR-T cells to infiltrate tumors, using G4HH2H3 sequence as a template to modify the hinge region by means of site-directed mutation.

The second object of the present invention is to provide a method for obtaining the hinge region amino acid sequence of SEQ ID NO:1 or SEQ ID NO: 2, the method comprises the amino acid sequence of the hinge region as shown in SEQ ID NO:1 is derived from humanized CD7 hinge structure, and the SEQ ID NO:2 is obtained by using PCR-mediated site-directed mutation, and the G4HH2H3 amino acid sequence is used as a template to modify the hinge region, the G4HH2H3 amino acid sequence is shown in SEQ ID NO:4.

Furthermore, hinge sequence G4HH2H3mt is obtained according to the method above, wherein the G4HH2H3mt is the amino acid sequence of G4HH2H3 comprises mutation and/or deletion at positions 15-18 and 79.

The third object of the present invention is to provide a modification method of the hinge region, the amino acid sequence of the hinge region as shown in SEQ ID NO:3 is a hinge sequence derived from a humanized CD8a amino acid sequence, in which cysteine at position 29 and cysteine at position 46 are modified, the modification method comprises random mutations and deletions; the hinge amino acid sequence derived from the humanized CD8a amino acid sequence is shown in SEQ ID NO:5.

Furthermore, the sequence of the hinge region is the hinge sequence derived from the humanized CD8a amino acid sequence, in which cysteine at position 29 and cysteine at position 46 are deleted.

The fourth object of the present invention is to provide a chimeric antigen receptor, wherein the chimeric antigen receptor comprises the amino acid sequence SEQ ID NO: 1 or SEQ ID NO:2 or SEQ ID NO:3 of the hinge region, the hinge region is 7H or G4HH2H3mt or 8H (dc).

Furthermore, the chimeric antigen receptor also comprises an antigen recognition region, a transmembrane region and an intracellular signal region.

Furthermore, the antigen recognition region of the chimeric antigen receptor can recognize antigens expressed by tumor cells, including but not limited to PSCA, PSMA, CD19, BCMA, CD123, CD20, CD22, CEA, EGFR, EGFRVIII, GPC3 or mesothelin antigen molecules.

The chimeric antigen receptor is able to recognize antigens expressed by tumor cells, including but not limited to, the above antigen molecules.

The fifth object of the present invention is to provide a chimeric antigen receptor targeting PSCA, the chimeric antigen receptor comprises single chain antibody, hinge region, transmembrane region and intracellular signal region of anti-human PSCA antigen, the hinge region is 7H or G4HH2H3mt and the amino acid sequence of which is shown in SEQ ID NO:1 or SEQ ID NO:2 or SEQ ID NO:3.

Furthermore, the single chain antibody of anti-human PSCA antigen is provided in the amino acid sequence as shown in SEQ ID NO:6 or SEQ ID NO: 7 or SEQ ID NO:26 or SEQ ID NO:27.

Furthermore, the transmembrane region is CD28TM or CD8TM, the amino acid sequence of the CD28TM is shown in SEQ ID NO:8, the amino acid sequence of the CD8TM is shown in SEQ ID NO:9, the intracellular signal region is CD28 and/or CD137 and/or CD3, the amino acid sequence of the CD28 is shown in SEQ ID NO: 10, the amino acid sequence of the CD137 is shown in SEQ ID NO: 11, the amino acid sequence of the CD3 is shown in SEQ ID NO:12.

Furthermore, the amino acid sequence of the chimeric antigen receptor is shown in SEQ ID NO: 13 or SEQ ID NO: 14 or SEQ ID NO: 15 or SEQ ID NO: 16 or SEQ ID NO: 17 or SEQ ID NO: 18 or SEQ ID NO:28 or SEQ ID NO: 29 or SEQ ID NO:30.

The chimeric antigen receptor can recognize the antigens expressed by tumor cells, including but not limited to the above antigen molecules.

The sixth object of the present invention is to provide a vector manufactured by the chimeric antigen receptor, the vector is lentivirus expression vector, retrovirus expression vector, adenovirus expression vector, adeno-associated virus expression vector, DNA vector, RNA vector or plasmid.

The manufacture method of the vector specifically comprises the following steps:

1) Synthetize nucleotide sequence of the chimeric antigen receptor targeting PSCA: Synthetize nucleic acid sequence of the chimeric antigen receptor including leader peptide, single chain antibody of anti-human PSCA antigen, hinge region, transmembrane region and intracellular signal region, the nucleic acid sequence of the leader peptide is shown in SEQ ID NO: 19, the nucleotide sequence of the hinge is shown in SEQ ID NO:20 or SEQ ID NO:21 or SEQ ID NO:32.

2) Construct a virus vector expressing the chimeric antigen receptor: Design primers, of which the nucleotide sequence of the forward primer is shown in SEQ ID NO: 22, the nucleotide sequence of the reverse primer is shown in SEQ ID NO: 23, take the nucleotide sequence of the chimeric antigen receptor as a template to perform PCR amplification to obtain a DNA fragment, package and purify the virus vector, the virus vector is lentivirus vector.

3) The nucleotide sequence of the DNA fragment is double digested with a restriction enzyme, and the virus expression vector pCDH-CAG is digested with a restriction enzyme at the same time, and then the target fragment and the virus expression vector fragment after enzyme cleavage are connected through T4 ligase to obtain the virus vector expressing chimeric antigen receptor.

The nucleotide sequence of the chimeric antigen receptor of step 1) is shown in SEQ ID NO:24 or SEQ ID NO:25 or SEQ ID NO:31.

The lentivirus vector is obtained by this method, the positive cells transduced by such a lentivirus vector have high expression ratio and stay stable during the course of culturing the patient cells and will not cause the CAR positive rate to decline over time. Cells infected with the lentivirus vector have the function of killing the target cells.

The seventh object of the present invention is to provide a cell infected by the vector, specifically the cell includes but not limited to T cells or NK cells or DC cells.

The eighth object of the present invention is to provide a use of the cell in the manufacture of a medicament for treatment of tumor.

To achieve the above objectives, the present invention takes the following solutions.

The present invention is to provide a use of the cell in the manufacture of a medicament for treatment of tumor, and the tumor cells or tissues can express PSCA.

The ninth object of the present invention is to provide a use, specifically a use of the hinge region amino acid sequence as hinge region in the construction of a CAR skeleton.

The amino acid sequence of the hinge region is shown in SEQ ID NO: 1 or SEQ ID NO:2 or SEQ ID NO:3.

In some embodiments, the modification of the hinge region derived from the humanized CD8α sequence can be directed to mutating the cysteine at position 29 and cysteine at position 46. In some embodiments, the hinge region of the chimeric antigen receptor may be mutating the cysteine at position 29 and/or cysteine at position 46 in SEQ ID NO:3 to glycine or alanine.

In some embodiments, the hinge region of the chimeric antigen receptor may be a sequence modified from the G4HH2H3 sequence, such as a chimeric antigen receptor that includes a hinge region that lacks the amino acid sequence of H2H3 segment of the G4HH2H3 sequence. In some embodiments, the hinge region sequence of the chimeric antigen receptor is the G4HH2H3 sequence without H2 segment. The specific sequence is shown in Table 1.

QVKLQESGGGLVQPGGSLKLSCVASGFTFSSYTMSWVRRTPEKRLEWVA

YIHNGGGHTYYPDTIKGRFTISRDNAKNTLFLEMSSLKSEDTAMYYCTR

RMYYGNSHWYFDVWGAGTSVTVSSGGGGSGGGGSGGGGSDIQMTQSPSS

LSASVGDRVTITCRTSQDISNYLNWYQQKPGKAPKLLIYYTLKLNSGVP

SRFSGSGSGTDFTFTISSLQPEDIATY YCQQSKTLPWTFGGGTKVEIK

In some embodiments, the amino acid sequence of an antibody that specifically recognizes PSCA is shown below (SEQ ID NO:27):

EVQLVESGGGLVQPGGSLRLSCAASGFNIKDYYIHWVRQAPGKGLEWVAW

IDPENGDTEFVPKFQGRATISADTSKNTAYLQMNSLRAEDTAVYYCKTGG

FWGQGTLVTVSSGGGGSGGGGSGGGGSDIQLTQSPSSLSASVGDRVTITC

SASSSVRFIHWYQQKPGKAPKRLIYDTSKLASGVPSRFSGSGSGTDFTLT

ISSLQPEDFATYYCQQWSSSPFTFGQGTKVEIK

In some embodiments, the amino acid sequence of an antibody that specifically recognizes PSCA is shown below (SEQ ID NO:40):

DIQLTQSPSSLSASVGDRVTITCSASSSVRFIHWYQQKPGKAPKRLIYDT

SKLASGVPSRFSGSGSGTDFTLTISSLQPEDFATYYCQQWSSSPFTFGQG

TKVEIKGSTSGSGKPGSGEGSTKGEVQLVESGGGLVQPGGSLRLSCAASG

FNIKDYYIHWVRQAPGKGLEWVAWIDPENGDTEFVPKFQGRATISADTSK

NTAYLQMNSLRAEDTAVYYCKTGGFWGQGTLVTVSS

TABLE 1

Modification of G4HH2H3 hinge region

| Name of hinge region | Hinge region sequence | Mutation and/or deletion site |
|---|---|---|
| G4HH2H3 (SEQ ID NO: 4) | ESKYGPPCPPCPAPEFLGGPSVFLFPPKPKDTLMI SRTPEVTCVVVDVSQEDPEVQFNWYVDGVEVH NAKTKPREEQFNSTYRVVSVLTVLHQDWLNGKE YKCKVSNKGLPSSIEKTISKAKGQPREPQVYTLP PSQEEMTKNQVSLTCLVKGFYPSDIAVEWESNGQ PENNYKTTPPVLDSDGSFFLYSRLTVDKSRWQEG NVFSCSVMHEALHNHYTQKSLSLSLGK | Position 15-18: EFLG Position 79: N |
| G4Hing (SEQ ID NO: 33) | ESKYGPPCPPCP | Deletion of H2H3 sequence |
| G4HH3 (SEQ ID NO: 34) | ESKYGPPCPPCPGQPREPQVYTLPPSQEEMTKNQ VSLTCLVKGFYPSDIAVEWESNGQPENNYKTTPP VLDSDGSFFLYSRLTVDKSRWQEGNVFSCSVMH EALHNHYTQKSLSLSLGK | Deletion of H2 sequence |

In some embodiments, the antigen recognition region of the chimeric antigen receptor comprising the hinge structure could be any polypeptide that can bind to PSCA antigen, such as ligands that can specifically bind to PSCA, bispecific antibodies, scFV, optional cross-linked Fab, F(ab)2, single region antibodies, and scFV connected with His-tag or HA-tag. In some embodiments, antibodies that specifically recognize PSCA are derived from 7F5; in some embodiments the amino acid sequence of the antigen recognition region is shown below (SEQ ID NO:26):

In some embodiments, the amino acid sequence of an antibody that specifically recognizes PSCA is shown below (SEQ ID NO:39):

DIQLTQSPSSLSASVGDRVTITCSASSSVRFIHWYQQKPGKAPKRLIYDT

SKLASGVPSRFSGSGSGTDFTLTISSLQPEDFATYYCQQWSSSPFTFGQG

TKVEIKGGGSGGGGSGGGGSSEVQLVESGGGLVQPGGSLRLSCAASGFN

-continued

IKDYYIHWVRQAPGKGLEWVAWIDPENGDTEFVPKFQGRATISADTSKNT

AYLQMNSLRAEDTAVYYCKTGGFWGQGTLVTVSS

In some embodiments, the chimeric antigen receptor comprising the hinge modified by the inventor is the second-generation chimeric antigen receptor, that is to say, the intracellular signal is CD28 signal and CD3 signal, or CD137 signal and CD3 signal. The specific sequence includes but not limited to the sequence shown in Table 2 below, wherein the amino acid sequences of serial number 1 and 2 are SEQ ID NO:29 and SEQ ID NO: 30, respectively.

TABLE 2

| | CAR combination with 8H(dc) hinge structure | |
|---|---|---|
| Serial NO. | CAR Sequence | intracellular signal |
| 1 (SEQ ID NO: 29) | DIQLTQSPSSLSASVGDRVTITCSASSSVRFIHWYQQKP GKAPKRLIYDTSKLASGVPSRFSGSGSGTDFTLTISSLQP EDFATYYCQQWSSSPFTFGQGTKVEIKGSTSGSGKPGS GEGSTKGSEVQLVESGGGLVQPGGSLRLSCAASGFNIK DYYIHWVRQAPGKGLEWVAWIDPENGDTEFVPKFQGR ATISADTSKNTAYLQMNSLRAEDTAVYYCKTGGFWGQ GTLVTVSSKPTTTPAPRPPTPAPTIASQPLSLRPEARPAA GGAVHTRGLDFADIYIWAPLAGTCGVLLLSLVITLYCVK RGRKKLLYIFKQPFMRPVQTTQEEDGCSCRFPEEEEGG CELRVKFSRSADAPAYQQGQNQLYNELNLGRREEYDV LDKRRGRDPEMGGKPRRKNPQEGLYNELQKDKMAEA YSEIGMKGERRRGKHDGLYQGLSTATKDTYDALHMQ ALPPR | CD137 and CD3 |
| 2 (SEQ ID NO: 30) | DIQLTQSPSSLSASVGDRVTITCSASSSVRFIHWYQQKP GKAPKRLIYDTSKLASGVPSRFSGSGSGTDFTLTISSLQP EDFATYYCQQWSSSPFTFGQGTKVEIKGSTSGSGKPGS GEGSTKGSEVQLVESGGGLVQPGGSLRLSCAASGFNIK DYYIHWVRQAPGKGLEWVAWIDPENGDTEFVPKFQGR ATISADTSKNTAYLQMNSLRAEDTAVYYCKTGGFWGQ GTLVTVSSKPTTTPAPRPPTPAPTIASQPLSLRPEARPAA GGAVHTRGLDFADFWVLVVVGGVLACYSLLVTVAFIIF WVRSKRSRLLHSDYMNMTPRRPGPTRKHYQPYAPPRD FAAYRSVKFSRSADAPAYQQGQNQLYNELNLGRREEY DVLDKRRGRDPEMGGKPRRKNPQEGLYNELQKDKMA EAYSEIGMKGERRRGKHDGLYQGLSTATKDTYDALH MQALPPR | CD28 and CD3 |
| 3 (SEQ ID NO: 37) | DIQMTQSPSSLSASVGDRVTITCRTSQDISNYLNWYQQ KPGKAPKLLIYYTLKLNSGVPSRFSGSGSGTDFTFTISSL QPEDIATYYCQQSKTLPWTFGGGTKVEIKGSTSGSGKP GSGEGSTKGQVKLQESGGGLVQPGGSLKLSCVASGFTF SSYTMSWVRRTPEKRLEWVAYIHNGGGHTYYPDTIKG RFTISRDNAKNTLFLEMSSLKSEDTAMYYCTRRMYYG NSHWYFDVWGAGTSVTVSKPTTTPAPRPPTPAPTIASQ PLSLRPEARPAAGGAVHTRGLDFADIYIWAPLAGTCGV LLLSLVITLYCVKRGRKKLLYIFKQPFMRPVQTTQEEDG CSCRFPEEEEGGCELRVKFSRSADAPAYQQGQNQLYNE LNLGRREEYDVLDKRRGRDPEMGGKPRRKNPQEGLYN ELQKDKMAEAYSEIGMKGERRRGKHDGLYQGLSTAT KDTYDALHMQALPPR | CD137 and CD3 |
| 4 (SEQ ID NO: 38) | DIQMTQSPSSLSASVGDRVTITCRTSQDISNYLNWYQQ KPGKAPKLLIYYTLKLNSGVPSRFSGSGSGTDFTFTISSL QPEDIATYYCQQSKTLPWTFGGGTKVEIKGSTSGSGKP GSGEGSTKGQVKLQESGGGLVQPGGSLKLSCVASGFTF SSYTMSWVRRTPEKRLEWVAYIHNGGGHTYYPDTIKG RFTISRDNAKNTLFLEMSSLKSEDTAMYYCTRRMYYG NSHWYFDVWGAGTSVTVSKPTTTPAPRPPTPAPTIASQ PLSLRPEARPAAGGAVHTRGLDFADFWVLVVVGGVLA CYSLLVTVAFIIFWVRSKRSRLLHSDYMNMTPRRPGPTRKHYQPYAPPRDFAA YRSVKFSRSADAPAYQQGQNQLYNELNLGRREEYDVL DKRRGRDPEMGGKPRRKNPQEGLYNELQKDKMAEAY SEIGMKGERRRGKHDGLYQGLSTATKDTYDALHMQA LPPR | CD28 and CD3 |

Beneficial Effects of The Present Invention

1) The hinge region structure provided by the present invention can prolong survival time of CAR-T cells in vivo.
2) The chimeric antigen receptor constructed by the hinge region structure provided by the present invention can be more stably expressed on T lymphocytes, and has better capability to clear tumor cells, which can not only maintain the positive rate of the PSCA-targeted chimeric antigen receptor in the process of patient cell culture, but also can enhance the CAR-T's capability to proliferate and kill tumors. It has no toxic and side effects on antigen-negative cells and can be used for targeted therapy of tumors.
3) The CAR-T cell comprising the hinge structure provided by the present invention has enhanced capability of infiltrating tumor tissue and can effectively kill solid tumor.

BRIEF DESCRIPTION OF DRAWINGS

FIG. 1 shows CAR structure diagram of different hinge regions and their composition.

FIG. 2 shows different hinge sequences, including SEQ ID NO: 1 (7H), SEQ ID NO:2 (G4HH2H3mt), SEQ ID NO:3 (8H (dc)), SEQ ID NO:4 (G4HH2H3) and SEQ ID NO:5 (8H).

EMBODIMENTS

Figure 3:
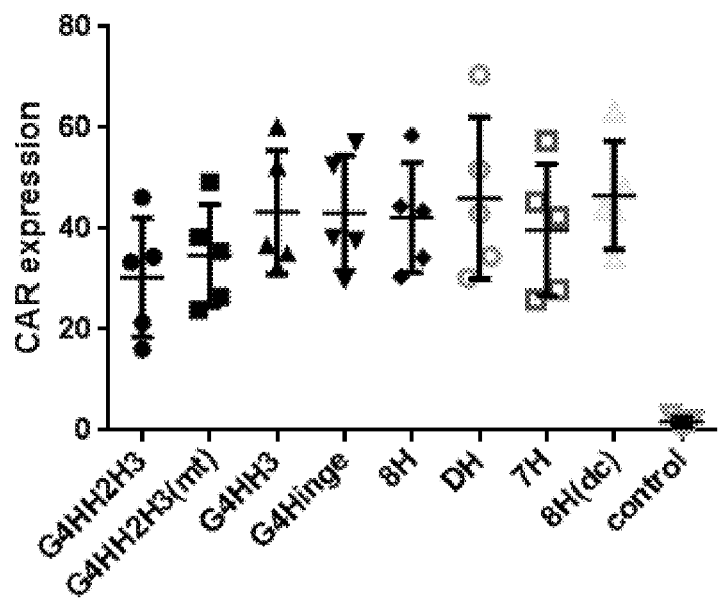
FIG. 3 shows CAR expression rate of different hinge region combinations.

The provided embodiments are intended to better describe the present invention, and not to limit the contents of the present invention to the embodiments. Accordingly, when a skilled artisan makes nonessential improvements and adjustments to the technical solution of the above invention, such improvements and adjustments shall still fall within the protection scope of the present invention.

Embodiment 1 Hinge Region Modification

Use the G4HH2H3 hinge region derived from IgG4FC sequence as a template. The hinge region was modified by means of site-directed mutation. 8H (dc) is a modified sequence obtained by deleting the cysteines at positions 29 and 46 in the commonly used hinge region 8H sequence. 7H and DH are the hinge region sequences derived from human CD7 and human IgD, respectively. The modification results are shown in FIG. 1 and FIG. 2. G4HH2H3mt is a modified sequence obtained by the G4HH2H3 mutation at the positions 15-17 and 79, and deletion at the position 18. G4HH3 is a sequence of deleting H2 segment. G4Hinge is obtained by deleting the H2H3 segment sequence. 8H (dc) is a modified sequence obtained by deleting the cysteines at positions 29 and 46 in the commonly used hinge region 8H sequence.

Embodiment 2 Construction of Chimeric Antigen Receptor Viruses with Different Hinge Regions In order to verify the effect of hinge regions of different structures on the survival of CAR-T in vivo and tumor infiltration, take PSCA-targeted CAR-T as an example. Design CARs with 8 different hinge structures as shown in FIG. 1.
1. Synthesis of PSCA-Targeted Chimeric Antigen Receptor Gene Sequence Containing the Above Designed Hinge Sequence.

Synthesis of CAR structures containing leader peptide (also called signal peptide, LP) and anti-human PSCA antigen single-chain antibody, 8 different hinge regions, CD28 transmembrane region (abbreviated as TM), and CD28, CD137 and CD3 intracellular signal regions.
2. Construction of Lentivirus Vector Expressing Chimeric Antigen Receptor.

Design the following primers and synthesize them by biotechnology companies. The specific primers are as follows:

Primer 1 (SEQ ID NO:22): 5'-atcgctag-catggccctgccagtgaccgcc-3', NheI restriction enzyme site is underlined.

Primer 2 (SEQ ID NO:23): 5'-ccaggtcgact-tagcgaggggggcagggcctg-3', SalI restriction enzyme site is underlined.

Then use the sequences shown above as primers, and each of the chimeric antigen receptor sequences synthesized above as a template for PCR amplification. Sample addition of the reaction system is performed according to KODFX NEO DNA polymerase (purchased from Toyobo company) instruction manual. After the amplification product is identified, the DNA fragment is recovered with a recovery kit (Promega company). For the specific method, see the instructions. The chimeric antigen receptor is recovered, and the DNA recovered fragment is sent to the biotechnology company for sequencing.

The cloned gene sequence encoding the chimeric antigen receptor is double-digested with restriction enzyme NheI and SalI (purchased from Thermo Company), and the lentivirus expression vector pCDH-CAG (purchased from addgene Plasmid) is digested with restriction enzyme NheI and SalI. The enzyme digestion reaction is performed according to the instructions. The digested products are separated by agarose gel electrophoresis, and the DNA fragments are recovered using the agarose gel DNA fragment recovery kit, and then the target fragments and the vector fragments are ligated by T4 ligase (purchased from Promega) to obtain the lentivirus vector expressing chimeric antigen receptor, named Lv-hinge. The lentivirus vector is transformed into *Escherichia coli* TOP10 and pick up monoclonal to culture for 12 hours, and plasmids are extracted with a plasmid extraction kit (Invitrogen company). See the instructions for specific methods.

Construct 8 lentivirus vectors as above method, respectively.

"scFv-8H hinge-CD28TM-CD28-CD137-CD3Z",

"scFv-8H (dc) hinge-CD28TM-CD28-CD137-CD3Z",

"scFv-7H hinge-CD28TM-CD28-CD137-CD3Z",
"scFv-DH hinge-CD28TM-CD28-CD137-CD3Z",
"scFv-G4HH2H3 hinge-CD28TM-CD28-CD137-CD3Z",
"scFv-G4HH2H3mt hinge-CD28TM-CD28-CD137-CD3Z",
"scFv-G4HH3 hinge-CD28TM-CD28-CD137-CD3Z",
"scFv-G4Hinge-CD28TM-CD28-CD137-CD3Z".

3. Lentivirus Packaging

In this embodiment, the lentivirus package uses calcium phosphate method. For specific steps, see the Molecular Cloning Experiment Guide (Third Edition, J. Sambrook et al.).

4. Lentivirus Purification

The virus supernatant is collected in a 50 ml centrifuge tube, filtrated by centrifugation, and the filtrate is centrifuged at 3000 r/min for 10 min and moved to a new 50 ml centrifuge tube; according to the amount of virus supernatant, add PEG6000 with a mass fraction of 50% and 4M NaCl respectively, and then use medical saline to adjust the final concentration of PEG6000 to 8.5% and the final concentration of NaCl to 0.3M. After the adjustment, store it in the refrigerator at 4° C., then centrifuge at 4° C. and discard the supernatant. The virus is resuspended in 200 μl DMEM medium, and divided into 1.5 ml EP tubes, each tube with 40 μl, and stored at −80° C. for future use.

5. Lentivirus Titer Determination

Step 1: Viruses Infect 293T Cells

Plate 293T cells before infection, take 1 μl of the purified virus, dilute it 10 times with medical saline, then add 1 μl of Polybrene solution to the cells inside each well, and then add the virus to 293T cells respectively. 24 hours after infection, change the solution with 10% FBS (wt) DMEM medium; 72 hours after infection, centrifuge at 1000 r/min for 5 min to collect the cells, and extract the genome.

Step 2: Extract Genome

The genomic extraction kit QIAamp DNA Blood Mini Kit is purchased from Qiagen Corporation (Product No. 511004), and operate according to the kit instructions.

Step 3: Determination of Virus Titer by qRT-PCR

Reaction system: Premix Ex Taq™ II (2×) 10 μl, Upstream primer (GAG up) 1 μl, Downstream primer (GAG dn) 1 μl, extracted genome 1 μl, RNase-Free dH$_2$O 7 μl, at least 3 replicate wells for each sample and standard solution. Then perform the amplification according to the following procedures: pre-denaturation at 95° C. for 30 s, denaturation at 95° C. for 5 s, annealing at 60° C. for 30 s, and extension at 72° C. for 30 s. After the reaction, analyze data with analysis software, and calculate virus titer based on a standard curve.

Embodiment 3 Detection of the Capability of CAR to Transfect T Lymphocytes

1 Isolation of Human Peripheral Blood Mononuclear Cells

Collect about 60 ml of peripheral blood with blood collection tube, dispense the blood into 50 ml centrifuge tube, add 7.5 ml of hydroxyethyl starch to dilute; settle naturally at room temperature (18-25° C.) for about 30 min and collect the upper plasma. After centrifuging the collected upper plasma, resuspend it with physiological saline, add it to lymphocyte separation solution at a volume ratio of 1:1, and then conduct gradient centrifugation.

After the centrifugation, the centrifuge tube is divided into: the first layer: plasma layer; the second layer: annular milky white lymphocyte layer; the third layer: transparent separation layer; the fourth layer: red blood cell layer. Take the second layer, annular milky white lymphocyte layer, wash it twice with normal saline, centrifuge for 5 min, resuspend the cells with normal saline, add RPMI 1640 complete medium containing 10% FBS and culture, to obtain human peripheral blood mononuclear cells.

2 Lentivirus Vectors Infect T Lymphocytes

Freshly prepared mononuclear cells PBMC are cultured in RPMI 1640 complete medium containing 10% fetal bovine serum, and PBMC activation is performed on the first day; lentivirus infection is performed on the third day. Add 5MOI corresponding lentivirus vector, and use uninfected T lymphocytes as blank control, replace the medium with RPMI1640 complete medium containing 500 IU/ml recombinant human IL-2 after 24 hours, and continue to culture for 10-20 days. Obtain CAR-T cells expressing the chimeric antigen receptor including antigen recognition region, hinge region, transmembrane region and intracellular signal region, named after the modified hinge region, named as: PSCA-CAR-G4HH2H3, PSCA-CAR-G4HH2H3mt, PSCA-CAR-G4HH3, PSCA-CAR-G4Hinge, PSCA-CAR-7H, PSCA-CAR-8H, PSCA-CAR-8H (dc) and PSCA-CAR-DH. In order to facilitate labeling when drawing, the above-mentioned CAR-T cells are abbreviated as G4HH2H3, G4HH2H3mt, G4HH3, G4Hinge, 7H, 8H, 8H (dc) and DH in subsequent embodiment and drawings of the specification.

1) During the culture process, the virus-infected T cells cultured to 10 days are centrifuged to discard the supernatant to collect the cells, resuspend the cells with a PBS solution containing a volume fraction of 1% fetal bovine serum, and adjust the cell density to 1×10$^6$ cells/ml. Sub-package the collected cells and detect the positive rate of Protein-L by flow cytometry. The test result indicates the positive rate of different CAR combinations expressed on T lymphocytes on the 10$^{th}$ day of culture. Simultaneous analysis of MFI (average fluorescence intensity) by flow cytometry to obtain the results of CAR average fluorescence intensity.

Figure 4:
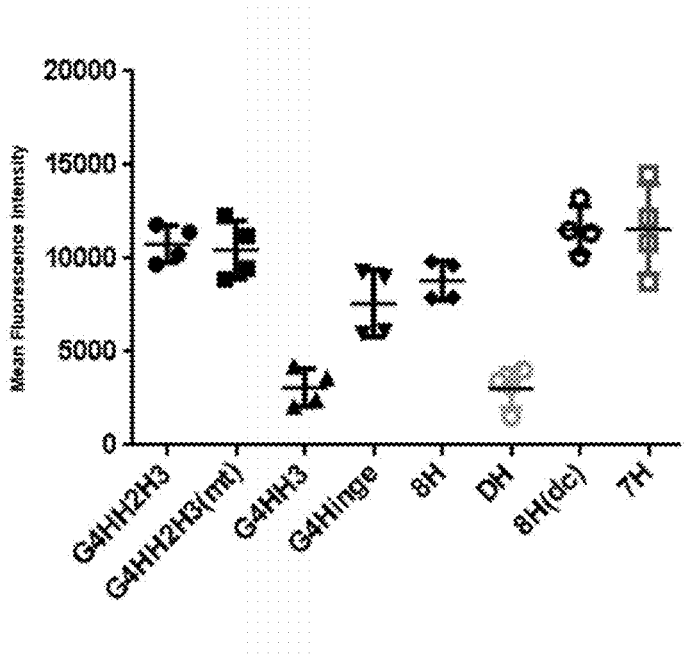
FIG. 4 shows CAR average fluorescence intensity detection of CAR-T cells with different hinge region combinations.

Results are shown in FIG. 3 and FIG. 4. The results of FIG. 3 show that the positive rate of modified hinge structure G4HH2H3mt, G4HH3, G4Hinge, 7H and DH combined CAR expression on the T cell surface is not much different from the conventional hinge G4HH2H3 or 8H combined CAR. FIG. 4 shows the average fluorescence intensity of CAR expression on the surface of CAR-T cells with different hinge structures. Among them, CARs with G4HH2H3, G4HH2H3mt, 7H or 8H (dc) structure can be highly expressed on the surface of T cells and have higher surface average fluorescence intensity, which indicates that CAR molecules are expressed more on the cell surface, and the surface average fluorescence intensity of the CARs with G4HH3, G4Hinge or DH structure are lower.

In summary, there is no significant difference as to the positive rates of CARs with G4HH2H3mt, G4HH3, G4Hinge, 7H and 8H (dc) hinge structures expression on the surface of T cells, but CARs with G4HH2H3mt, 7H and 8H (dc) structures have higher surface average fluorescence intensity and are more sensitive to antigens, and the CAR-T data required to achieve the expected killing effect will also be lower.

2) Detection of CAR expression of different hinge structure combinations on the 5$^{th}$, 10$^{th}$, and 14$^{th}$ days after infection and acquisition of CAR-T cells by the method of step 1), and detection of the stability of CAR expression after long-term culturing.

Figure 5:
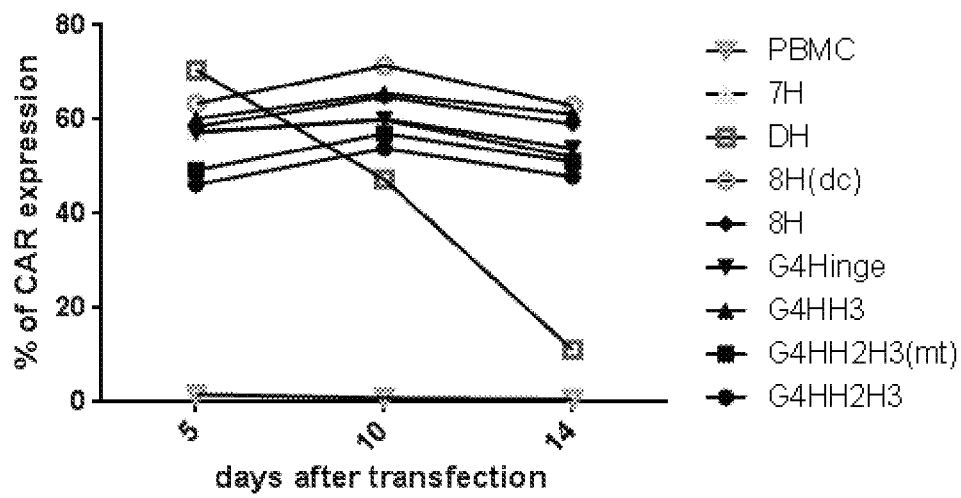
FIG. 5 shows CAR expression stability detection of CAR-T cells with different hinge region combinations.

Results are shown in FIG. 5: the long-term expression of CAR is tested and found that, when the modified structure is compared with the unmodified structure G4HH2H3 and 8H, the CAR expression stability of the DH hinge structure is poor. The positive rate of CAR decreased significantly after the 5$^{th}$ day and decreased even more significantly with the extension of culture time. The CAR stability of the remaining modified hinge structures and the unmodified hinge combination have no significant difference, among which, 8H (dc) has higher CAR expression, and long-term expression is also relatively more stable.

Embodiment 4 Detection of Long-Term Proliferation Capability of CAR-T Cells

Detection of proliferation of the infected PSCA-CAR-T cells under normal culture conditions; CAR-T cells obtained in the embodiment 3 are cultured for 10 days using the method in Step 2 of the embodiment 3. PSCA antigen coated 24-well plate for overnight at 4° C., CAR-T cells are plated with 1×10$^6$/well on the PSCA antigen coated 24-well plate to observe the survival time of CAR-T cells after antigen stimulation. On the 3$^{rd}$, 6$^{th}$, 9$^{th}$, and 12$^{th}$ days after stimulation, count the number of CAR-T cells with a cell counter and calculate CAR-T cells proliferation multiples. Results are shown in FIG. 6.

Based on the experience of in vivo experiments, antigen stimulation is performed once every 7 days. The results of FIG. 6 showed that the CAR-T cells no longer proliferated after the third stimulation of the antigen, so the experiment is terminated after the 15$^{th}$ day, after the third stimulation. Calculate the CAR-T long-term proliferation multiples and the survival time of long-term proliferation response of CAR-T cells.

Figure 6:
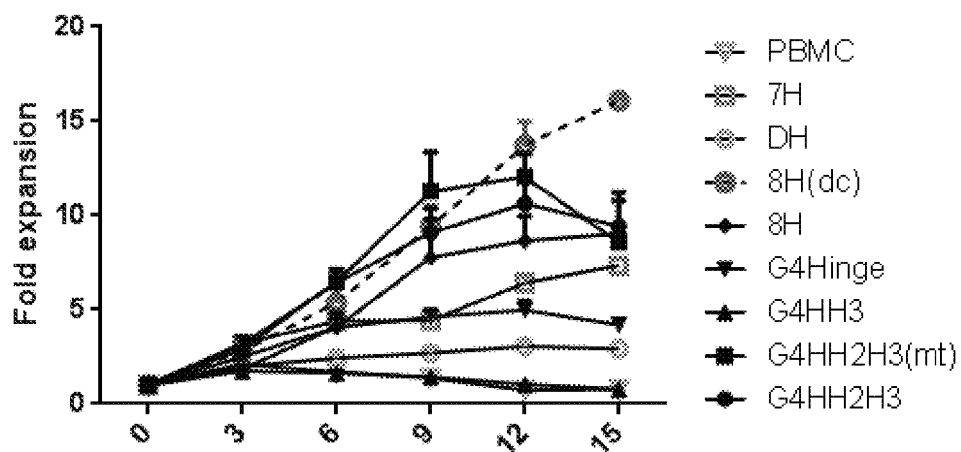
FIG. 6 shows long-term proliferation of CAR-T cells with different hinge region combinations.

Results are shown in FIG. 6. CAR-T cells with G4HH2H3, G4HH2H3mt, 8H, 7H, and 8H (dc) hinge combination proliferate relatively faster in the long term and CAR-T cells have stronger survivability in vitro. CAR-T cells with DH, G4Hinge, and G4HH3 have poor long-term proliferation capability.

In summary, CAR-T cells with G4HH2H3, G4HH2H3mt, 7H, 8H, and 8H (dc) hinge combination proliferate relatively faster, and CAR-T cells have stronger survivability in vitro.

Embodiment 5 Effects on the Capability of CAR-T Cells to Eliminate Tumor Cells

The killing capability of CAR-T with different hinge structures on target cells is measured by ACEA xCELLigence RTCA MP instrument, and the experimental procedure is carried out according to the instrument manual.

The target cells (PSCA-expressing tumor cells) are plated with 2-5×10$^4$/well in 96-well plate equipped with the instrument on the first day, the tumor cells attached to the bottom of the well are recorded every 15 minutes using the resistance index as the data. After 24 hours, the corresponding CAR-T cells are plated in each well according to the pre-designed efficiency-target ratio, and the resistance index is recorded every 15 minutes after the CAR-T cells are plated, and the resistance index is used to determine the proliferation or death of the adherent target cells. The formula used for analyzing the resistance index analysis result: CAR-T cell killing rate=baseline resistance index-real-time resistance index.

HeLa and RT4 are tumor cell lines with high expression of PSCA, T24 are negative control cells without PSCA expression.

Figure 7:
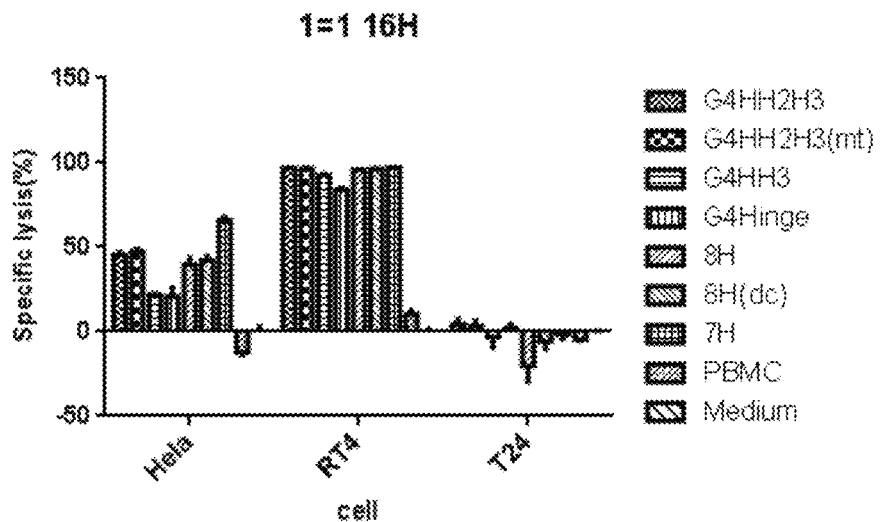
FIG. 7 shows the killing rate of CAR-T cells in vitro with different hinge region combinations.

Results are shown in FIG. 7, G4HH2H3, G4HH2H3mt, 8H, and 8H (dc) have better killing capability, and do not kill negative cells, and accordingly have strong specificity.

Subsequently, CAR-T cells containing G4HH2H3, G4HH2H3mt, 8H, 7H and 8H (dc) hinge structures are used for in vivo experimental verification.

Embodiment 6 Verification of Anti-Tumor Effects of CAR-T Cells in Animal Models

Establishment of a mouse xenograft model of human PSCA positive tumor cell line to verify the antitumor effect of T lymphocytes in animal model, wherein the T lymphocytes express chimeric antigen receptor targeting PSCA.

In vivo verification, the mouse used is NOD.Cg-PrkdcscidIl2rgtm1Sug/JicCrl, abbreviated as NOG mouse, which is bred by Mamoru Ito of Japan Institute of Experimental Animals (CIEA) and is the most common strain used in CAR-T in vivo related tumorigenesis experiments in the world. The tumorigenesis target cells used in the in vivo verification is Hela (abbreviated as Hela-luc), a PSCA-positive cell line stably expressing firefly luciferase, which is used in the previous in vitro verification.

The previous in vitro experiments found that the modified hinge G4HH2H3, G4HH2H3mt, 7H, 8H and 8H (dc) structures have better killing and in vitro survivability, therefore, in animal experiments, the 5 types of CAR-T cells (including the commonly used CAR-T cells with G4HH2H3 and 8H hinges) are used to measure the capability to kill tumors in mice. The therapeutically injected effector cells are CAR-T cells containing G4HH2H3mt, G4HH2H3, 7H, 8H (dc) and 8H hinge structures, and the control is saline group, non-infected PBMC cells.

Figure 8:
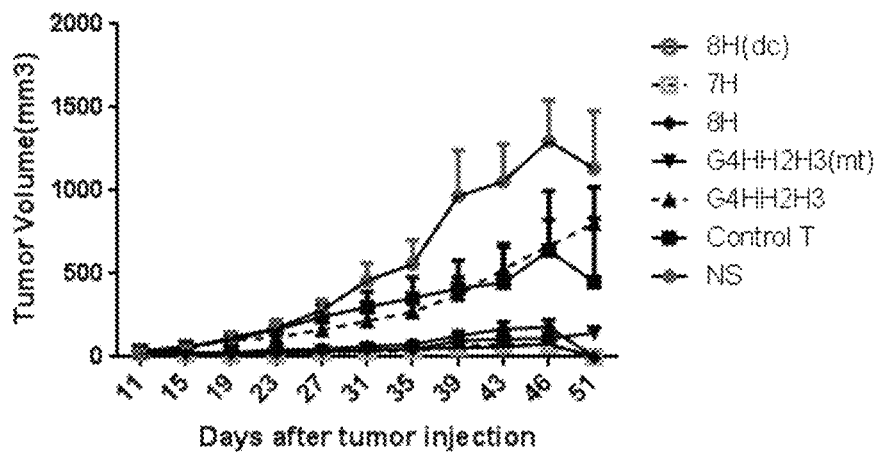
FIG. 8 shows a comparison of the killing effect of CAR-T cells with different hinge region combinations in vivo.
Figure 9:
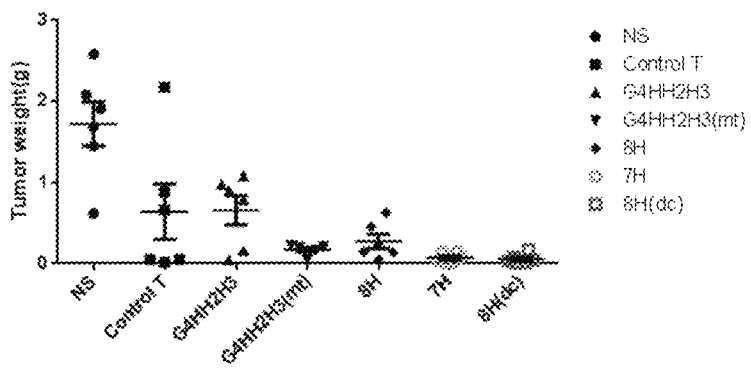
FIG. 9 shows result of tumor weight after CAR-T cells killing in vivo, the CAR-T cells with different hinge region.

Inject effector CAR-T cells into tail vein after tumorigenesis, at 5×10$^5$ cells/mouse. After injection of the CAR T cells, images are taken every 7 days by PerkinElmer's IVS in vivo imaging system to show tumor growth. During the period, observe and record the survival of the mice every day. Results are shown in FIG. 8: CAR-T cells containing G4HH2H3mt, 7H, 8H (dc) and 8H hinges have good killing effect on tumor cells in vivo. After the mice are killed at the end of the experiment, the tumor tissues are removed and weighed, and the results are statistically analyzed, as shown in FIG. 9: mice treated with CAR-T cells containing G4HH2H3mt, 7H, and 8H (dc) hinges have lighter tumor weight, especially mice treated with CAR-T cells containing 7H and 8H (dc) hinge combination have been basically free of tumor.

Embodiment 7 Study on the Survival and Tumor Infiltration Capability of CAR-T Cells In Vivo Use RT-PCR to detect CAR gene copies in tumor issue to detect the survival capability of CAR-T cells in vivo and the tumor infiltration capability of CAR-T cells in vivo.
1. Design Primers

```
BBZ-HF:
                                (SEQ ID NO: 35)
CAGAAGAAGAAGAAGGAGGATGTG;

BBZ-HR:
                                (SEQ ID NO: 36)
TACTCCTCTCTTCGTCCTAGATTG.
```

2. Extract RNA from Tumor Issue

Firstly, add liquid nitrogen to the mortar, then cut the tumor tissue into small pieces and grind them into powder in liquid nitrogen. Use a spatula pre-cooled with liquid nitrogen to take an appropriate amount of tissue powder and add it to the EP tube containing Trizol solution and mix sufficiently well. Place at room temperature for 5 min, then add 200 ml of chloroform, cover the EP tube tightly and shake vigorously for 15 s. Centrifuge it and take the upper water phase into a new EP tube, add 500 ml of isopropanol, mix gently by inverting. Centrifuge it at room temperature for 10 min. Discard the supernatant carefully, add 1 ml of 75% ethanol, vortex to mix, centrifuge it and repeat the operation once. Discard the supernatant and dry at room temperature or vacuum for 5 to 10 minutes. Dissolve RNA in 30 ml DEPC treated water, store in 70% ethanol and store at −70° C.

3. RT-PCR

Perform RT-PCR, the reaction system is as follow:

Reaction system: Forward primer (10 μM) 0.5, Reverse primer (10 μM) 0.5 μl, 2×SYBR Premix Ex Taq II 10 μl, Template 1 μl, Extracted genome 1 μl, RNase-Free dH$_2$O 7 μl, at least 3 replicate wells for each sample and standard solution. Then perform amplification according to the following procedure: 95° C. for 2 min, 95° C. for 15 s, 60° C. for 1 min, 40 cycles. After the reaction, analyze the data with analysis software. The analysis results are shown in Table 3 and FIG. 10.

Figure 10:
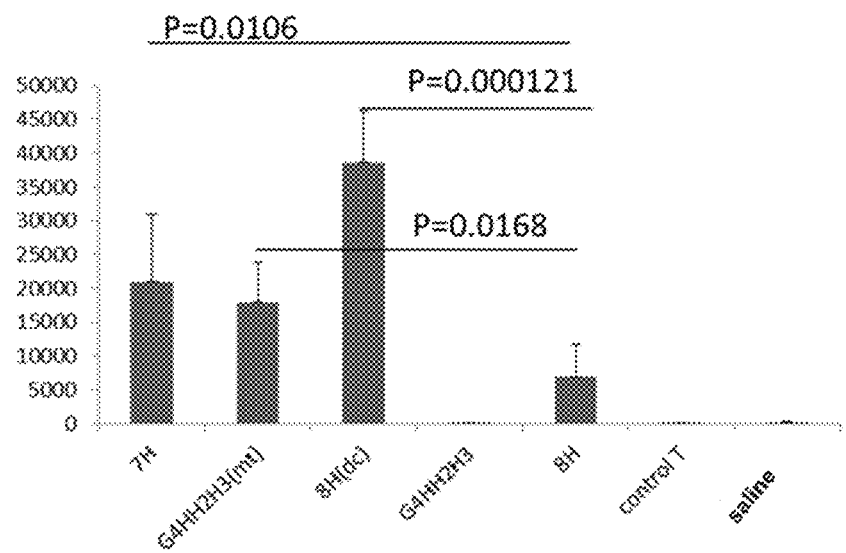
FIG. 10 shows study on the survival of CAR-T cell in vivo and tumor infiltration capability of different hinge region combinations.

Table 3 shows the detected CAR copies of tumor tissues treated with CAR T cells of different structures, and FIG. 10 is a graph drawn according to the results of Table 3. The results show that 7H, G4HH2H3mt and 8H (dc) as hinge areas can significantly enhance the capability of CAR-T to infiltrate the tumors.

TABLE 3

45 days after the reinfusion of the CAR-T cells, the survival time of CAR-T with different hinge structures in vivo

| Group | Copies/ug | | | | | | Copies Mean |
|---|---|---|---|---|---|---|---|
| 7H | 25334.120 | 10407.800 | 7653.580 | 34199.720 | 24571.460 | 23548.740 | 20952.570 |
| G4HH2H3mt | 13892.010 | 10027.970 | 24928.830 | 20763.770 | 20069.680 | | 17936.452 |
| G4HH2H3 | 39.210 | 285.580 | 92.580 | 39.540 | 44.040 | 19.290 | 86.707 |
| control T | 25.750 | 18.240 | 35.970 | 10.430 | 347.070 | 8.550 | 74.335 |
| 8H | 14989.200 | 8645.350 | 2296.620 | 8370.480 | 2344.560 | 4683.690 | 6888.317 |
| 8H(dc) | 36473.150 | 34065.390 | 52071.950 | 36012.530 | 34429.970 | | 38610.598 |
| Saline | 46.690 | 20.460 | 367.280 | 53.200 | 35.050 | | 104.536 |

Lastly, it should be clarified that the above embodiments are just to elaborate the technical solution of the present invention and are not to limit the same. While the present invention has been described in details with reference to the preferred embodiments, it should be further appreciated by the person skilled in the art that modifications and equivalent replacements of the technical solution of the present invention do not fall out of the objective and scope of the technical solution of the present invention, and should be covered within the claims of the present invention.

The invention claimed is:

1. A chimeric antigen receptor, comprising a hinge region consisting of the amino acid sequence of SEQ ID NO:3, antigen recognition region, transmembrane region and intracellular signal region; wherein the antigen recognition region is able to recognize antigen expressed by tumor cells, wherein the antigen is PSCA.

2. The chimeric antigen receptor according to claim 1, wherein comprising single chain antibody of anti-human PSCA antigen, provided in the amino acid sequence as shown in SEQ ID NO:6 or SEQ ID NO:7 or SEQ ID NO: 26 or SEQ ID NO:27.

3. The chimeric antigen receptor according to claim 2, wherein the transmembrane region is CD28TM or CD8TM, the amino acid sequence of the CD28TM is shown in SEQ ID NO:8, the amino acid sequence of the CD8TM is shown in SEQ ID NO:9, the intracellular signal region is CD28 and/or CD137 and/or CD3, the amino acid sequence of the CD28 is shown in SEQ ID NO:10, the amino acid sequence of the CD137 is shown in SEQ ID NO:11, the amino acid sequence of the CD3 is shown in SEQ ID NO:12.

4. The chimeric antigen receptor according to claim 1, wherein the amino acid sequence of the chimeric antigen receptor is shown in SEQ ID NO: 28 or SEQ ID NO:29 or SEQ ID NO:30.

5. A vector expressing the chimeric antigen receptor according to claim 1.

6. The vector according to claim 5, wherein the vector is lentivirus expression vector, retrovirus expression vector, adenovirus expression vector, adenoassociated virus expression vector, DNA vector, RNA vector or plasmid.

7. A cell infected by the vector according to claim 5, wherein the cell is T cell or NK cell or DC cell.

* * * * *